United States Patent [19]

Shaw et al.

[11] Patent Number: 6,080,182
[45] Date of Patent: Jun. 27, 2000

[54] SELF-EXPANDING DEFECT CLOSURE DEVICE AND METHOD OF MAKING AND USING

[75] Inventors: Edward E. Shaw; Nitin V. Salunke; Gregory T. Mace, all of Flagstaff, Ariz.

[73] Assignee: Gore Enterprise Holdings, Inc., Newark, Del.

[21] Appl. No.: 08/995,097

[22] Filed: Dec. 19, 1997

Related U.S. Application Data

[63] Continuation-in-part of application No. 08/771,718, Dec. 20, 1996, Pat. No. 5,879,336.

[51] Int. Cl.$^7$ .................................................... A61B 17/04
[52] U.S. Cl. ........................ 606/213; 606/215; 128/887; 128/898
[58] Field of Search .................................. 606/151, 157, 606/213, 215, 158; 128/887, 898; 623/11

[56] References Cited

U.S. PATENT DOCUMENTS

| | | | |
|---|---|---|---|
| 5,334,217 | 8/1994 | Das | 606/213 |
| 5,433,727 | 7/1995 | Sideris | 606/213 |
| 5,725,552 | 3/1998 | Kotula et al. | 606/213 |
| 5,853,422 | 12/1998 | Huebsch et al. | 606/213 |
| 5,925,060 | 7/1999 | Forber | 606/191 |
| 5,944,738 | 8/1999 | Amplatz et al. | 606/213 |

FOREIGN PATENT DOCUMENTS

| | | |
|---|---|---|
| 94/07560 | 4/1994 | WIPO . |
| 95/27448 | 10/1995 | WIPO . |
| 97/28744 | 8/1997 | WIPO . |

OTHER PUBLICATIONS

Technical Information: BioInterventional™ Corporation, "Company Overview"/"Illustration Sequence Depicting Use Of The DISC–Closure–SURE™ Vascular Access Management System" (Date Unknown).

*Primary Examiner*—Gary Jackson
*Attorney, Agent, or Firm*—David J. Johns

[57] ABSTRACT

The present invention relates to a self-expanding device for sealing a defect in a wall, such as a septal defect. The device of the present invention has a fluoropolymer membrane that is supported by an embedded wire structure having elastic properties which is capable of being compressed and inserted in the defect by a catheter and thereafter returning to its memory induced configuration. The device of the present invention can be employed in a variety of applications where a small hole needs to be sealed.

41 Claims, 38 Drawing Sheets

FIG. 15A                    FIG. 15B

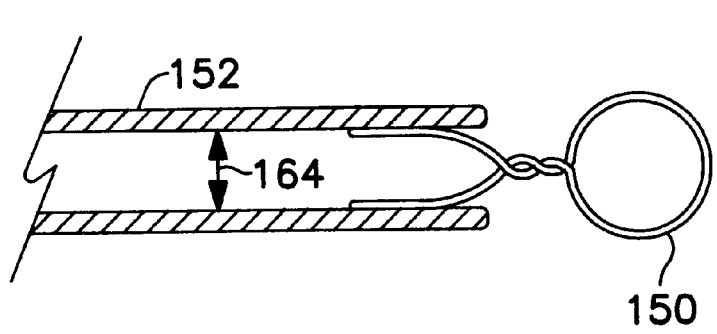
FIG. 23A
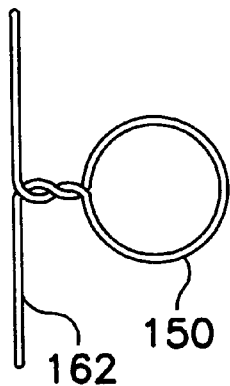
FIG. 23B
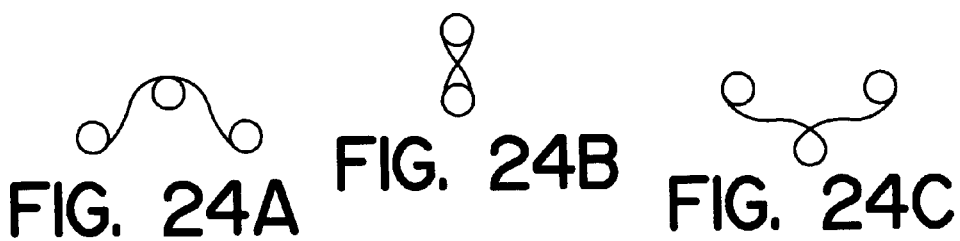
FIG. 24A  FIG. 24B  FIG. 24C
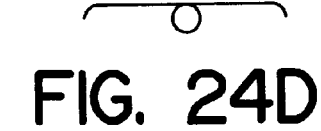  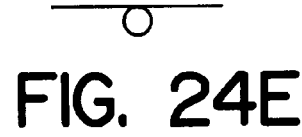
FIG. 24D  FIG. 24E
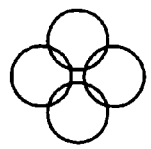  
FIG. 24F  FIG. 24G FIG. 35A
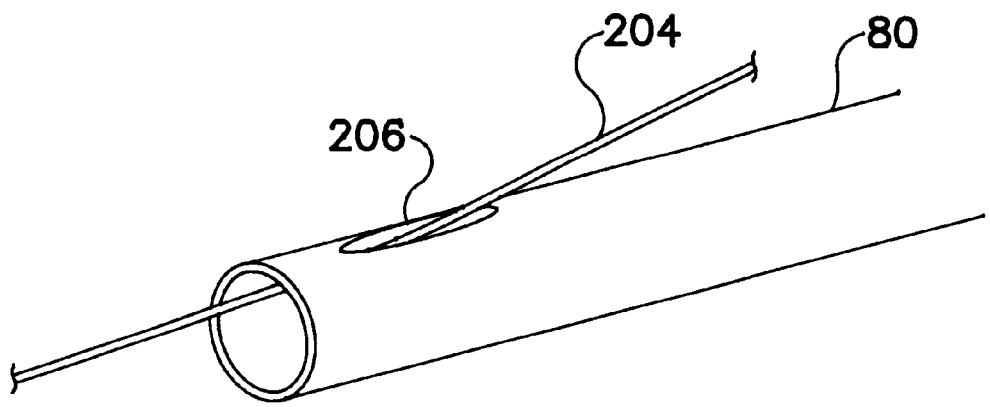
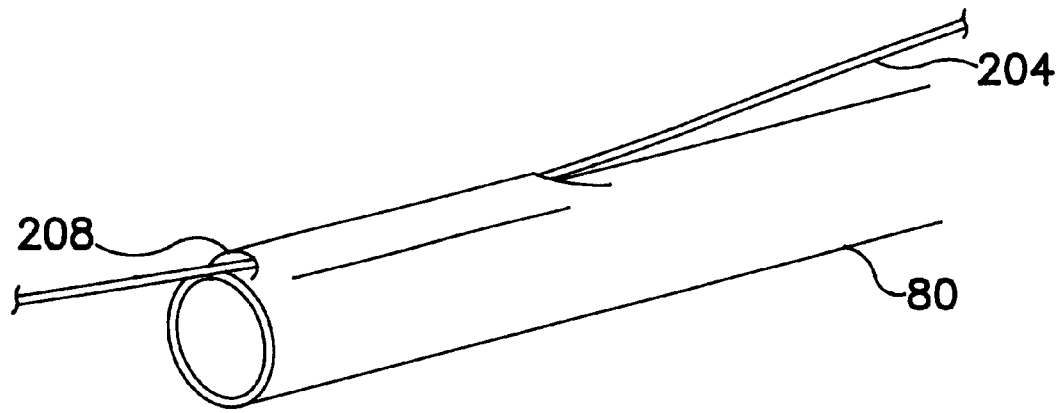
FIG. 35B

SELF-EXPANDING DEFECT CLOSURE DEVICE AND METHOD OF MAKING AND USING

RELATED APPLICATIONS

The present application is a continuation-in-part of co-pending U.S. patent application Ser. No. 08/771,718, filed Dec. 20, 1996 U.S. Pat. No. 5,879,336.

FIELD OF THE INVENTION

The present invention relates to closure devices, their manufacture and use to occlude a defect in a tissue or muscle of a living animal, such as a human being, or a defect in a wall of a structure, such as a container or filter. More specifically, the present invention relates to a self-expanding closure device having a membrane that is supported by a structure having elastic properties, which is capable of being compressed or collapsed and inserted through a defect, and thereafter returned to its memory induced configuration to cover or seal the defect.

BACKGROUND OF THE INVENTION

A wall defect is generally a hole in the wall of the tissue of a living animal, such as humans, or a hole in the wall of a container, tank, bag filter, or planar filter, tent, inflatable device, etc. In muscles or tissues of living animals, repairs have been accomplished by inserting an occlusion or septal closure device into the aperture or defect. Such devices include those taught by U.S. Pat. Nos. 5,334,217 to Das and 5,108,420 to Marks.

The Das patent describes a septal defect closure device, its use and method of assembly, where individual disks of a thin flexible material are supported by a super-elastic material and are used to occlude a wall defect. The disks are conjointly attached to one another at the center of the disk. The thin flexible material used in the Das patent can include nylon, polyester, polypropylene and polytetrafluoroethylene (PTFE) polymers. The super-elastic material is a NiTi alloy, such as nitinol.

The super-elastic material of the Das patent is formed into a frame having several legs and can assume geometrical configurations such as triangles, hexagons, circles, and stars. A membrane is wrapped around the legs of the frame. The loops between adjacent legs bias the legs outwardly, to form a concave membrane surface, which is maintained in a highly tensioned fashion.

The Marks patent describes an occlusion device that can be transported via a catheter in a compressed state. Once through the aperture to be occluded, the device is released and wires supporting two membranes are positioned on each side of the aperture. A domed or umbrella shaped configuration is formed and the support wires urge the membranes towards one another and the wall where the aperture is located.

These prior devices have numerous drawbacks. The support frames of the Das patent include resilient wire loops where leg ends of the frame meet and are attached to one another. The loops generally extend beyond the periphery of the membrane and can irritate or damage adjacent muscle or tissue.

Similarly, the exposed wires of the Marks device act as an irritant to tissue or muscle adjacent the aperture or septum. Here the bare sharp ends of the wire structure can further cause tissue erosion.

The Das and Marks patent devices use a membrane of conventional thickness that when folded over a wire add undesired thickness to the device. Additionally, the patents rely on peripheral membrane support which leaves the central occlusion covering portion of the membrane vulnerable.

In the Das patent design, each leg is provided with a bend at the middle of its length. This bend can add a tendency to the device to fold when the frame is sitting against a very flexible tissue and the membrane is pressurized by the blood. This may be the potential mechanism of failure as reported by Agarwal, et al. (1996). Agarwal, S. K., Ghosh, P. K. and Mittal, P. K., "Failure of Devices Used for Closure of Atrial Septal Defects: Mechanisms and Management," *The Journal of Thoracic and Cardiovascular Surgery*, Vol. 112, No. 1, 1996.

Finally, none of the previously available devices have provided a sufficiently small enough insertion diameter and/or collapsed flexibility. These limitations have restricted the utility and ease of use of such devices.

Thus, in view of the above, a need exists for a closure device that eliminates or significantly minimizes the traumatizing effect of existing closure devices. Further, a need exists for a device which is stable under physiological loading conditions when situated against the anatomical tissue structure. A need also exists for a defect closure device that is collapsible or compressible so that it may fit into a 9 F (9 French), preferably 5 F or 4 F or smaller catheter for deployment in a defect.

A need also exists for a closure device that is able to occlude or close wall defects in structures such as containers, tanks, tents, inflatable devices or filters without removing the structure from its environment of use. The present invention can meet these needs.

SUMMARY OF THE INVENTION

The present invention provides a self-expanding defect closure device that overcomes the many drawbacks and disadvantages of prior devices. The devices of the present invention rely on memory induced support structures having curved outer surfaces that minimize tissue erosion. These structures facilitate repair of septal defects. Also, these structures facilitate repair of other wall defects, such as in filters or containers or the like, without their removal from their environments of use. The device of the present invention can also be used with adhesives to repair the walls of tents, fabrics, inflatable devices, etc.

The structures of the present invention radially and circumferentially support a membrane, providing greater central support to the membrane. Thin membranes are laminated together and embed a memory induced elastic wire structure, preferably a super-elastic wire, to reduce the collapsed dimensions of the closure device. Thinner membranes are possible because the thin ply expanded polytetrafluoroethylene (ePTFE) films are cross-laminated to increase membrane strength and maintain a desired microstructure.

The support structure may have a star or helical geometrical configuration. The self-expanding defect closure device of the present invention can be readily deployed by a 9 F, preferably 5 F, or smaller catheter or thoracoscopic instrument or open procedural tools. These catheter sizes include 9.0 F, 8.5 F, 8.0 F, 7.5 F, 7.0 F, 6.5 F, 6.0 F, 5.5 F, 5.0 F, 4.5 F, 4.0 F, 3.5 F, 3.0 F, 2.5 F, 2.0 F and smaller.

An aspect of the present invention is to provide a closure device having one or two discrete sections where each section has a smoothly curved outer periphery and is formed from a single elastic element.

It is a purpose of the present invention to provide a self-expanding closure device that eliminates or minimizes trauma to existing muscles or tissues surrounding a defect to be occluded.

It is another purpose of the present invention to prepare a closure device by forming a wire structure into a desired configuration and inducing memory of that configuration into the wire, and laminating the wire structure so as to be embedded in the membrane.

It is another aspect of the present invention to manufacture a closure device. Thus it is a purpose of the present invention to manufacture a device by using cross ply laminated expanded PTFE films by: providing a first cross-ply membrane portion; locating an elastic wire on an upper surface of said first membrane portion; locating a second cross-ply membrane portion on an exposed surface of said wire and in contact with said upper surface of said first membrane portion; and affixing said first and second membrane portions to one another to embed said wire therebetween.

It is another purpose to manufacture a closure device by using cross ply laminated expanded PTFE films by: providing a cross laminated membrane; locating a heat resistant tube on said membrane; folding and laminating said membrane about said heat resistant tube; inserting an elastic wire into said heat resistant tube; and removing said heat resistant tube and heating said membrane to embed said elastic wire.

It is a further purpose of the present invention to deploy the subject closure devices in walls of containers or filters by providing a delivery tube; compressing and inserting the device into the delivery tube; deploying the compressed device in a defect; and inserting and releasing the device in the wall defect.

Another aspect of the present invention is to insert the closure device in a 9 F, preferably 5 F, or smaller catheter and deploy that device in a wall defect in a living animal.

These and other aspects and advantages will become more apparent when considered with the following detailed description, drawings and appended claims.

BRIEF DESCRIPTION OF THE DRAWINGS

FIG. 6 (B) shows a side view of the closure device, as the device is being collapsed.

FIG. 6 (C) shows a side view of the closure device, in a fully collapsed or small diameter state.

FIG. 9 (B) shows the heat-treated, memory induced helix shaped wire structure of the present invention, with the thermoplastic bonding agent coating the wire.

FIG. 9 (C) shows the cross section of the helical wire, with the thermoplastic bonding agent coating the wire.

FIG. 23 shows a latch means for sealing member securing and sealing member to sealing member securing.

FIGS. 24 (A) through (G) show alternate designs for the latch means for sealing member securing and sealing member to sealing member securing.

FIGS. 35 (A) and (B) show a delivery tube for use with the present invention that includes means to provide a guide wire.

DETAILED DESCRIPTION OF THE INVENTION

Figure 1:
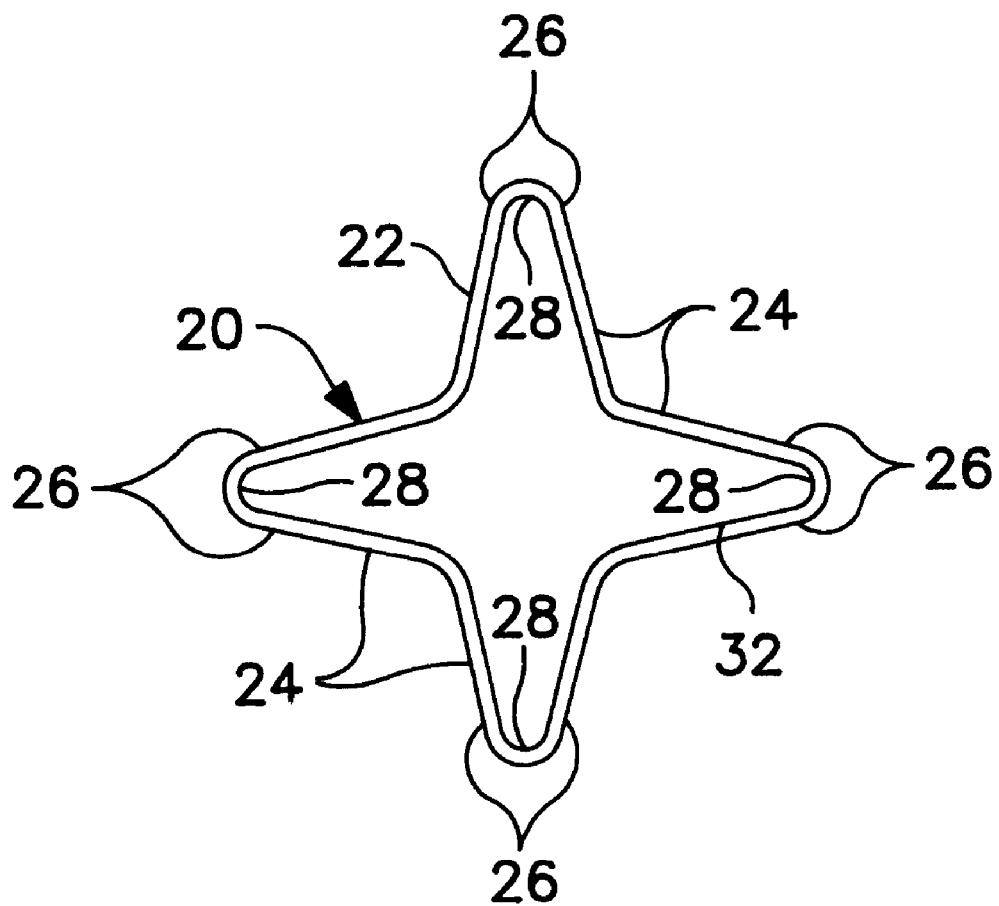
FIG. 1 shows the heat-treated, memory induced star shaped wire structure of the present invention.

The defect closure devices of the present invention are composite assemblies of support structures and membranes. For biological applications, the biocompatible membranes, such as expanded polytetrafluoroethylene (ePTFE). Such membranes block the defect, for example a septal defect, in the living animal and occlude the blood flow. This device can also be used to repair a variety of wall defects, either by remote or direct deployment.

A wall defect can be remotely repaired in a fluid containing vessel without draining the fluid. Other wall defects in contact with hazardous materials or environments can be remotely repaired. In addition, those defects where access is limited due to confined spaces or submersion, can also be remotely repaired. Direct deployment can be used to repair wall defects in those cases where access is non-restricted or limited by the immediate environment.

The supporting wire structures that are used in the devices according to the present invention have elastic properties that allow for them to be collapsed for catheter based delivery or thoracoscopic delivery, and self-expand to a "memory" induced configuration once positioned in a wall defect. The elastic wire may be a spring wire, or a shape memory NiTi alloy wire or a super-elastic NiTi alloy wire (generally referred to herein as "nitinol"). Upon deployment the wire structure resumes its deployed shape without permanent deformation.

The supporting structures of the present invention are formed from elastic wire materials that have diameters between about 0.12 and 0.4 mm. In one embodiment of the present invention the wire is about 0.2 mm in diameter and formed from nitinol.

The membrane that is used in the defect closure devices to occlude the flow of blood can be manufactured from a variety of materials, such as DACRON® polyester, polyethylene, polypropylene, fluoropolymers, polyurethane foamed films, silicone, nylon, silk, thin sheets of super-elastic materials, woven materials, polyethylene terephthalate (PET), pericardium tissue or any other biocompatible material. In one embodiment of the present invention, the membrane material is a fluoropolymer, in particular, expanded polytetrafluoroethylene (ePTFE) having a node-fibril structure. The membrane used in the present invention is manufactured from thin films of expanded PTFE that are each approximately 0.0025 to 0.025 mm thick. Thus, the films could be 0.0025, 0.005, 0.0075, 0.01, 0.0125, 0.015, 0.175, 0.02, 0.0225 and 0.025 mm thick.

From 1 to about 200 plys (layers) of expanded PTFE film are stacked up and laminated to one another to obtain a membrane with the desired mechanical and structural properties. An even number of layers are preferably stacked together (e.g., 2, 4, 6, 8, 10, etc.), with approximately 2 to 20 layers being desirable. Cross-lamination occurs by placing superimposed sheets on one another such that the film drawing direction, or stretching direction, of each sheet is angularly offset by angles between 0 degrees and 180 degrees from adjacent layers or plies. Because the base expanded PTFE is thin, as thin as 0.0025 mm or less in thickness, superimposed films can be rotated relative to one another to improve the mechanical properties of the membrane. In one embodiment of the present invention the membrane is manufactured by laminating together 8 plies of expanded PTFE film, each film ply being 0.0125 mm thick. In another embodiment of the present invention the membrane is manufactured by laminating together 4 plies of expanded PTFE film, each film ply being 0.0125 mm thick. The laminated expanded PTFE sheets are then sintered together at temperatures of about 370° C., under vacuum to adhere the film layers to one another. The resultant 8 ply laminate structure is typically about 0.04 mm thick.

The invention will now be described by reference to the figures and non-limiting embodiments. As shown in FIG. 1, a star shaped wire frame 20 for a defect closure device is prepared from a super-elastic wire material 22. A wire 22 of nitinol is fixtured in a jig (not shown) into a shape of a star 20. Star 20 has four arms 24, although different arm configurations may be employed, such as providing more arms (e.g., 5, 6, 7, 8, etc.). Each star 20 is preferably formed from a single wire that is configured to be star shaped, although multiple wires may be used. The star 20 includes eight legs 26 which terminate into four curved arcuate ends 28. The arcuate portion 28 extends over an angle that is less than 360°, and is connected to the distal ends of legs 26.

The star shaped wire 20 is constrained in a jig (not shown) and the combination is placed into an oven, heated for at least two minutes, up to about one-half hour, at about 400° to 600° C., e.g., 500° C. The star shaped wire 20 is cooled by air, water or any other means, and removed from the restraining jig. As the result of the 500° C., 30 minute heat treatment, the nitinol wire 22 obtains a memory induced configuration, which in this case is the shape of a star. The star shaped wire 20 exhibits super-elastic properties, which act to return the wire to the star shape even after extreme deformation, such as that shown in FIGS. 6 (A) through 6 (C).

Figure 2:
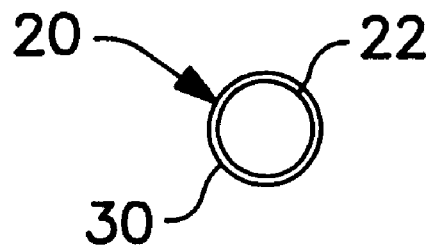
FIG. 2 shows a cross section of the wire in FIG. 1, with the thermoplastic bonding material coating the wire.

As shown in FIG. 2, the cross section of the star shaped wire 20 is coated with a bonding agent 30, for example fluorinated ethylene propylene (FEP) or other suitable polymer. A close tolerance FEP tube is slipped over the star shaped wire 20, so that the ends of the FEP tube are offset from the wire termination point 32 (FIG. 1). The FEP 30 will then be heated and adhered to the wire 22 during subsequent processing. The FEP coating can also be applied by dipping, spraying, laminating between sheets, or any other means. The two ends of the formed wire are attached together at the termination point 32 in FIG. 1, by welding, by crimping a sleeve onto the wire ends, or any other means.

Figure 3:
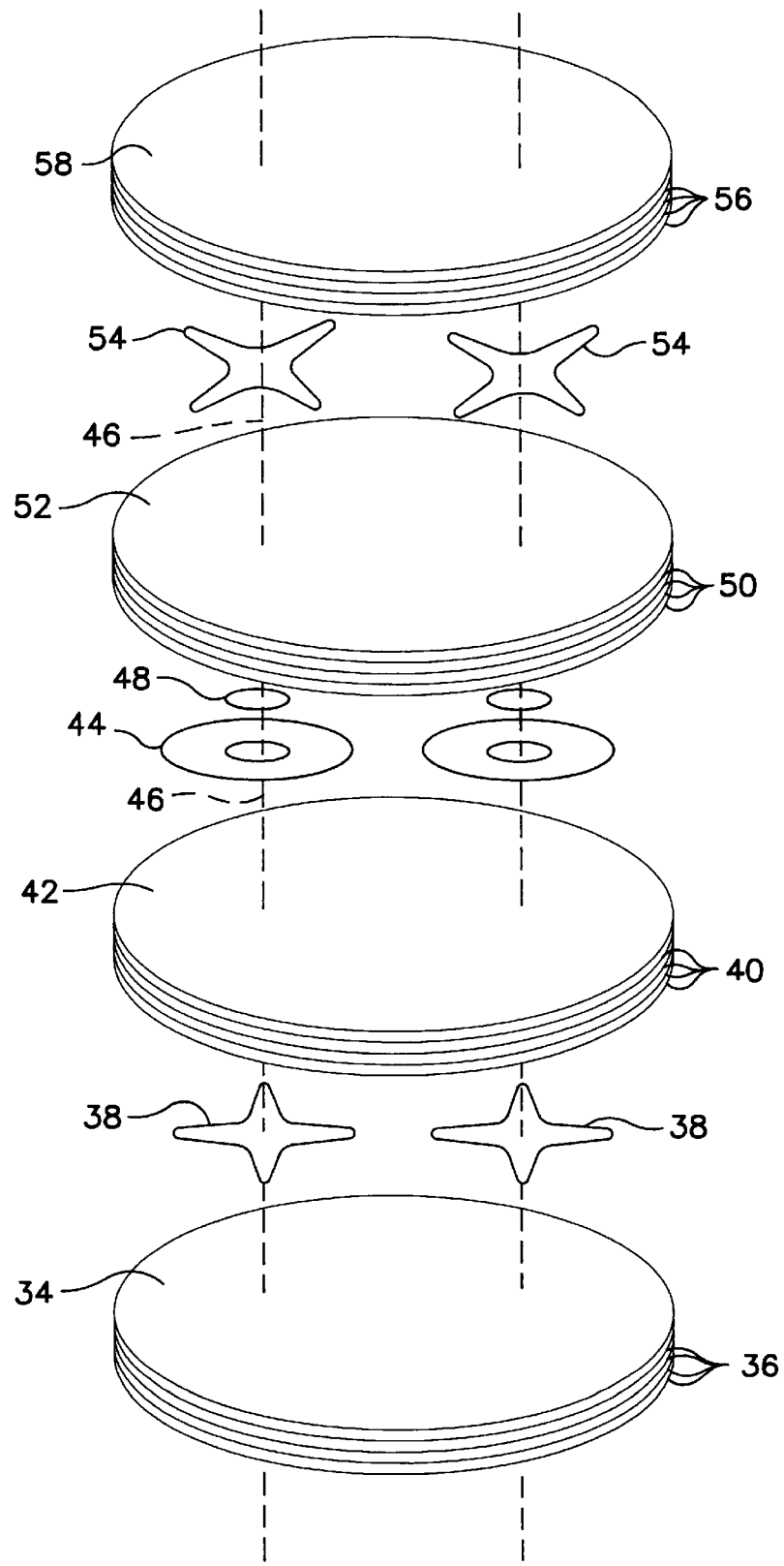
FIG. 3 shows an exploded assembly view of a complete laminate structure for a star shaped closure device where two complete devices are shown, both being fabricated together.

FIG. 3 shows an exploded assembly view of the closure device according to the present invention. A four ply laminate 34 is prepared from four film layers (plies) 36 of expanded PTFE. The film layers 36 are placed onto a porous vacuum chuck (not shown) with each film layer 36 being rotated about 90 degrees relative to one another. The four ply laminate 34 can be disk shaped, or any other suitable shape.

One or more FEP coated star shaped wire structures 38 are placed onto the four ply laminate 34. Four additional layers of expanded PTFE film 40, rotated about 90 degrees relative to each other, are placed onto the assembly, forming a second four ply laminate structure 42, with the FEP coated wire structures 38 embedded between the two four ply laminates 34 and 42.

A KAPTON® or other high temperature plastic ring 44 is aligned over the center axis 46 of each star shaped embedded wire 38. A disk of FEP 48 or other suitable bonding polymer is placed into the center of each ring 44. The FEP disk 48 is sized to fit within the central opening of the ring 44. The ring is sized such that the perimeter is larger than the star shaped wire 38.

Four additional film layers of expanded PTFE 50, rotated about 90 degrees relative to each other, are placed onto the assembly, forming a third four ply laminate 52. A second pair of FEP coated star shaped wire structures 54 are aligned to the central axis 46 and rotated about 45 degrees relative to the first embedded star shaped structures 38, and placed onto the third four ply laminate 52. Four additional film layers of expanded PTFE 56, rotated about 90 degrees relative to each other, are placed onto the assembly, forming a fourth four ply laminate 58, with the second FEP coated wire structures 54 embedded between the third four ply laminate 52 and fourth four ply laminate 58.

This entire assembly is then covered with a sheet of KAPTON® or other high temperature plastic (not shown), and placed into a sintering press (not shown). The sintering press constrains the edges of the laminate assembly from contracting and applies vacuum through the porous vacuum chuck to the assembly. Sintering is conducted at temperatures of about 370° C. for a period of several minutes, e.g., 15 minutes, up to several hours. The sintered assembly is cooled and the KAPTON® sheet is removed and discarded.

Figure 4:
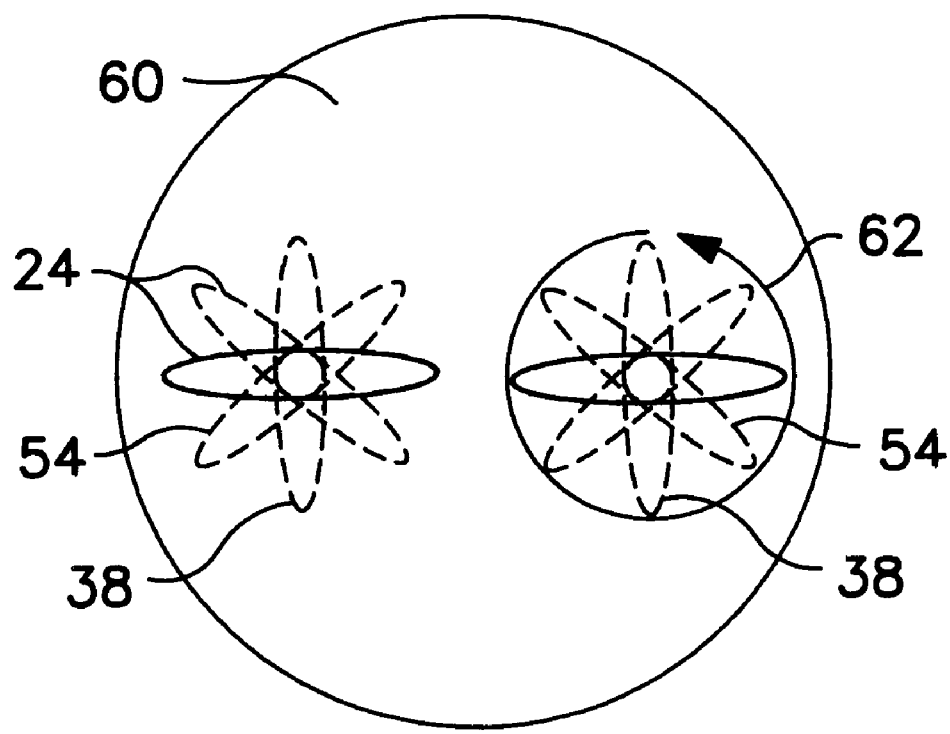
FIG. 4 shows the final laminate sheet and cutting pattern, containing two star shaped closure devices.

As shown in FIG. 4, the embedded star shaped wire structures 38 and 54 are then cut out of the laminated assembly 60 by laser, steel rule die, or any other means, per the cut pattern 62. The arms 24 of stars 38 and 54 radially support the laminated structure in a "relaxed" manner. In other words the laminated structure is not placed under tension by the arms 24 of star 38 and 54, when in the uncompressed or deployed state. The rings 44 (FIG. 3) are removed after the cutting operation.

Figure 5:
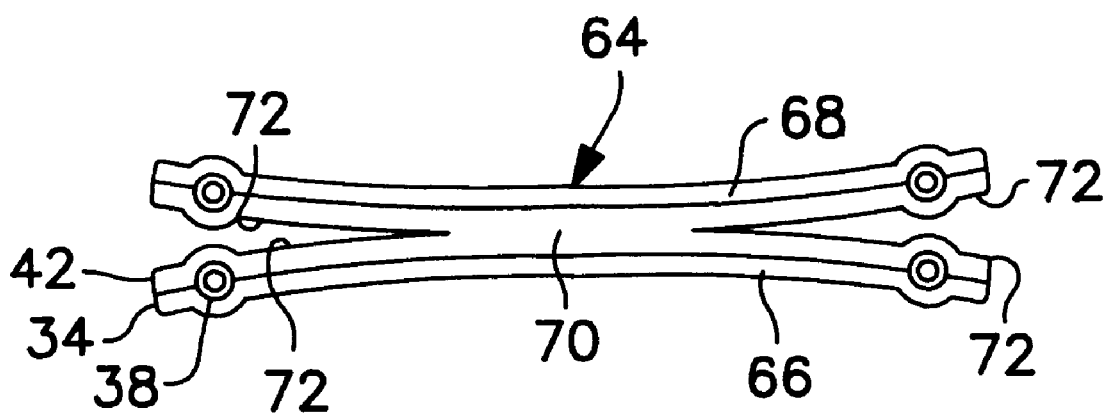
FIG. 5 shows a cross sectional view of a final closure device, detailing the central attachment point between the two membranes.

FIG. 5 shows a cross sectional view of the final closure device 64. Two of the four ply laminate structures 34 and 42 have been sintered together, embedding the FEP coated wire 38 to form a membrane 66. As previously described, the completed device includes a second identical membrane 68. The attachment point 70 between the two membranes is formed by the bonding polymer 48 (e.g., FEP) (FIG. 3), melting and reflowing during the sintering process. This attachment can also be accomplished by suturing, ultrasonic welding, or any other means of attaching the two membranes together. The non-attached surfaces 72 between the two membranes 66 and 68 are a result of the ring 44 (FIG. 3), which prevented complete membrane to membrane attachment during the sintering process.

Figures 6A, 6B, 6C:
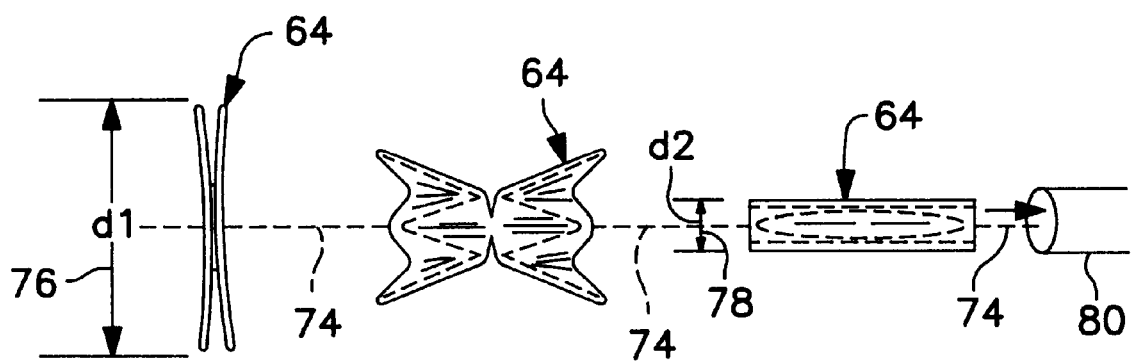
FIG. 6 (A) shows a side view of a closure device of the present invention in a deployed or large diameter state.

FIG. 6 (A) shows a side view of a closure device 64, with a longitudinal axis 74, in the deployed or large diameter state 76 having a diameter $d_1$.

FIG. 6 (B) shows a side view of a closure device 64, with a longitudinal axis 74, as the device is being collapsed.

FIG. 6 (C) shows a side view of a closure device 64, with a longitudinal axis 74, in the fully collapsed or small diameter state 78 having a diameter $d_2$, where $d_2$ is less than $d_1$, the ratio of $d_1:d_2$ being less than about 50:1, depending on the final deployed diameter $d_1$ of the device. The ratio of $d_1:d_2$ should be between about 5:1 and about 50:1, with a ratio of about 10:1 to about 50:1 being preferred (such as, 15:1, 20:1, 25:1, 30:1, 35:1, 40:1, 45:1.) Once in the collapsed state, the device can be inserted along the longitudinal axis 74 into a delivery tube 80. Thus the device has a compressed insertion configuration and an enlarged deployed configuration.

Figure 7A:
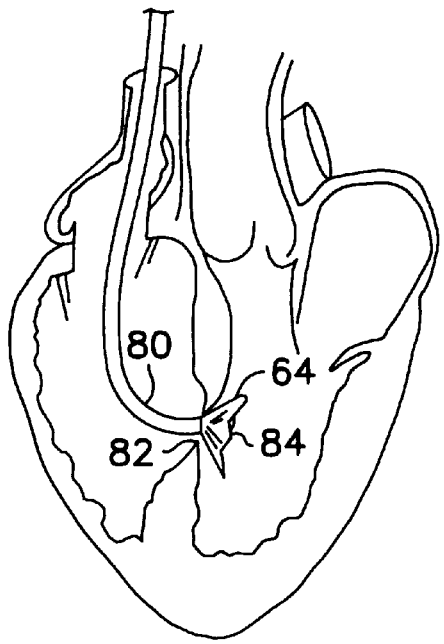
FIGS. 7 (A) through (C) show a star shaped defect closure device according to the present invention being positioned and deployed in a heart defect.
Figure 7B:
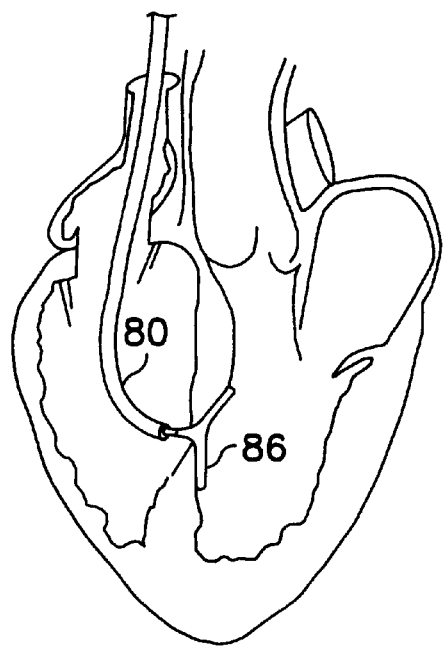
Figure 7C:
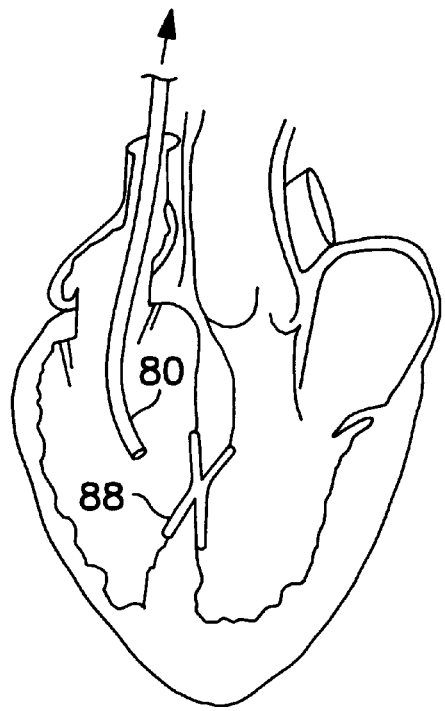
Figure 8A:
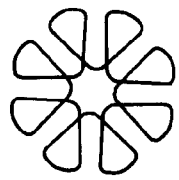
FIGS. 8 (A) through (F) show other configurations of generally star shaped, memory induced wire structures of the present invention.
Figure 8B:
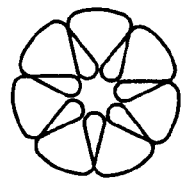
Figure 8C:
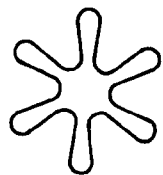
Figure 8D:
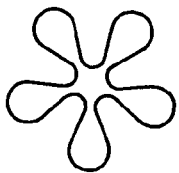
Figure 8E:
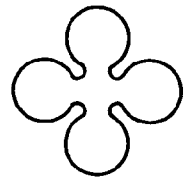
Figure 8F:
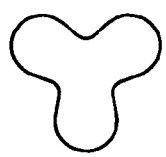

FIGS. 7 (A) through (C) show the deployment of the star closure device 64. A catheter or delivery tube 80 is loaded with closure device 64 and deployed in a defect 82. As seen in FIG. 7 (A), the distal side of the star device 84 expands when released from the catheter 80. As shown in FIG. 7 (B), the distal side of the star device assumes its memory induced shape 86, which approximates $d_1$ of FIG. 6 (A) 76. As shown in FIG. 7 (C), as the catheter 80 is further withdrawn, the proximal side of the device 88 is deployed, which also assumes its memory induced position.

FIGS. 8 (A) through (F) show other configurations of star wire structures. The fabrication of a closure device using one of these alternate star configurations is similar to the process used in the initial star device. The number of laminate layers can be varied to achieve the desired thickness and mechanical properties, and the cutting patterns adjusted to produce the desired deployed diameter or shape.

Figure 9A:
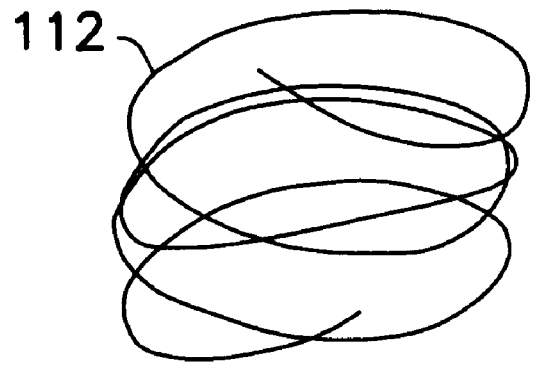
FIG. 9 (A) shows the heat-treated, memory induced helix shaped wire structure of the present invention.
Figure 9B:
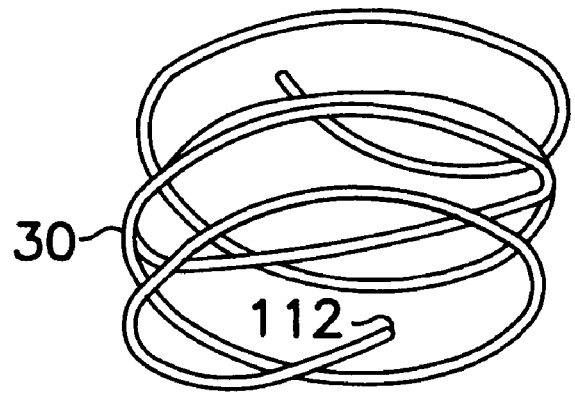
Figure 9C:
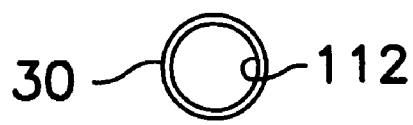

An alternate embodiment for closing an aperture according to the present invention is the helical design. As shown in FIG. 9 (A), nitinol wire 112, is placed in a constraining jig (not shown) and wound into the desired helical shape. This coiled, helically shaped wire, while being restrained in the jig (not shown), is placed in a heat treating oven and is subjected to the same "memory" inducing treatment as described before. Upon cooling and/or quenching, the coiled nitinol wire exhibits super-elastic properties which act to return the wire to the coiled, i.e., helical shape, even after extreme deformation, such as extending the wire into a linear configuration. A helical shape can include any shape that forms at least a partial outer periphery and has a longitudinal length. For example a helical shape can include a coil with varying or consistent diameters and angles. The outer periphery of the helical shape can include straight as well as arced segments.

As shown in FIG. 9 (B), the helical shaped wire 112 is coated with a bonding agent 30, for example a fluoroethylene polymer (FEP) or other suitable polymer. A close tolerance FEP tube 30 is slipped over the helical shaped wire 112. The FEP tube 30 is then heated and adhered to the wire 112 during subsequent processing. The FEP coating can also be applied by dipping, spraying, laminating between sheets, or any other means. FIG. 9 (C) shows a cross section of the wire 112 coated with polymer 30.

Figure 10A:
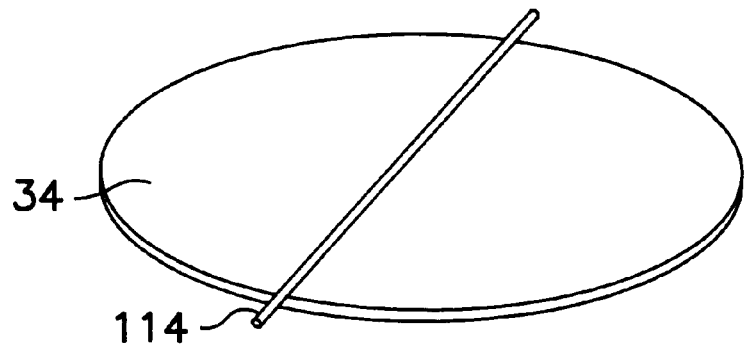
FIGS. 10 (A) through (C) show a multi-ply laminate being folded over a heat resistant stainless steel tube during the helical device fabrication process.
Figure 10B:
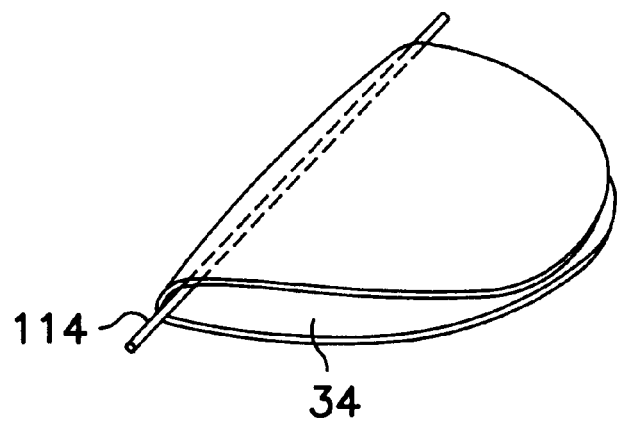
Figure 10C:
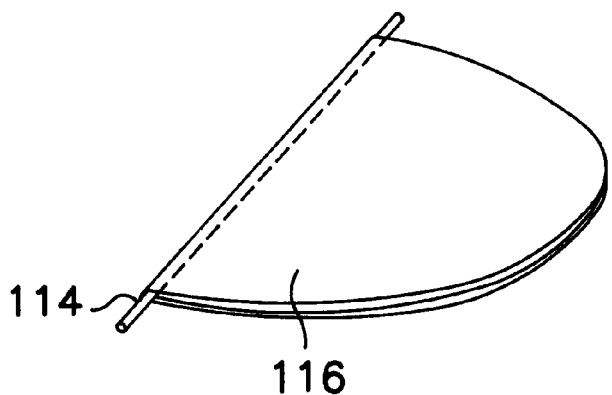

FIG. 10 (A) shows a multi-ply laminate 34 prepared from, for example, four film layers (plies) of expanded PTFE. The film layers are placed onto a porous vacuum chuck (not shown) with each film layer being rotated about 90 degrees relative to one another. The four ply laminate 34 can be disk shaped or any other shape. A high temperature tube 114 is placed on the center line of the four ply laminate 34.

FIG. 10 (B) shows the multi-ply laminate 34 being folded over the high temperature tube 114, forming a folded laminate which surrounds the tube.

FIG. 10 (C) shows the folded laminate. Since the four ply laminate has been folded once, the tube 114 is now embedded within an eight ply laminate, or membrane 116. This laminate assembly, with the embedded tube, is capped with a KAPTON® sheet and placed into a sintering press. As discussed above, the edges of the laminate are constrained, vacuum is applied to the assembly through the porous chuck, and the assembly heated to sintering temperatures. The temperature and time for the sintering process is the same as that described above for the star shaped configuration. The sintered assembly is cooled and the KAPTON® sheet is removed and discarded.

Figure 11:
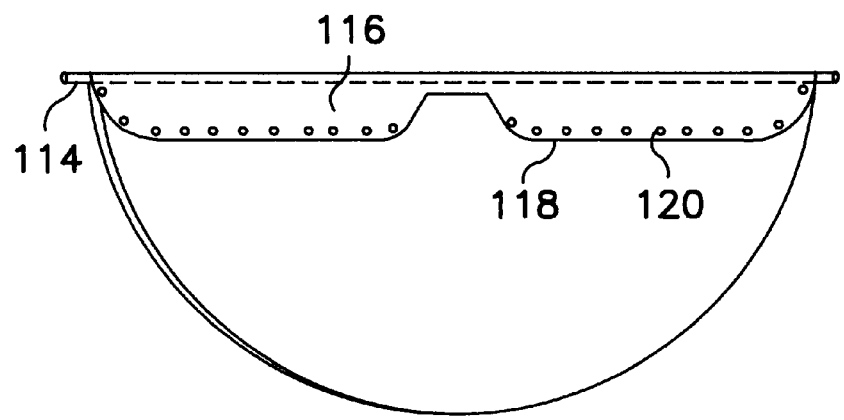
FIG. 11 shows the final laminate sheet, cutting pattern and suture hole pattern for the helical closure device.

FIG. 11 shows the laminate assembly, or membrane 116, high temperature tube 114, outline cutting 118 and suture hole patterns 120. The outline and suture holes are cut by laser, steel rule die, or any other means.

Figure 12:
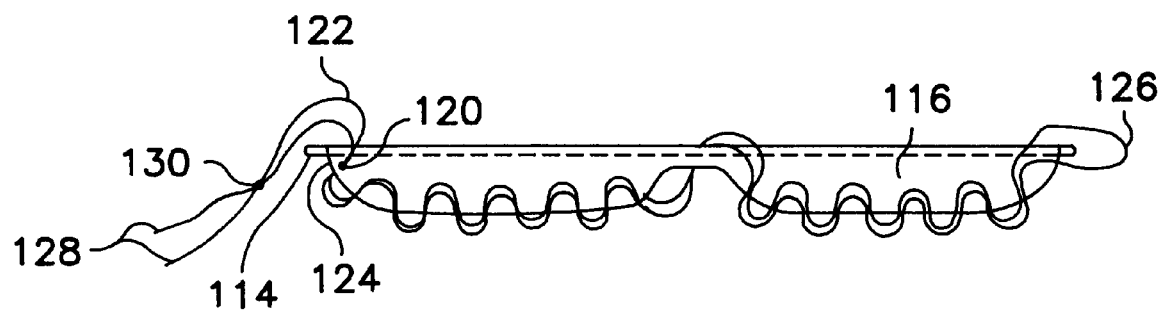
FIG. 12 shows the final laminate with the suture lacing pattern.

FIG. 12 shows a suture threading pattern for the laminated assembly 116. A single suture 122 is threaded from the left edge 124, through the pre-cut holes 120. After the first pass, the suture is folded back upon itself, forming a "bend" 126, and threaded in a reverse pattern through pre-cut holes, returning to the left edge 124. The two suture ends 128 are tied with a single knot 130. The helical wire 112 (FIG. 9 (C)), with the FEP coating 30 (FIG. 9 (C)), is tensioned into a linear shape and inserted into the high temperature tube 114. The high temperature tube 114 is removed from the laminated assembly 116, leaving the FEP coated wire captured within the laminated assembly. The laminated assembly and the captured wire are then heated to the FEP melting point, reflowing the FEP, which bonds the wire to the expanded PTFE membrane.

Figure 13:
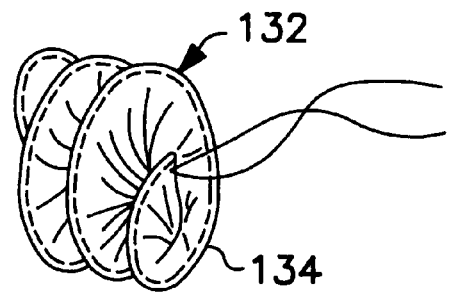
FIG. 13 shows an isometric view of a helical closure device, in the deployed or large diameter state.

FIG. 13 shows the completed helical closure device 132 in the deployed, relaxed or memory induced, large diameter state 134. The ratios of large to small diameters can be substantial, such as between 10:1 to 100:1, as defined by the star shaped configuration, FIGS. 6 (A) through (C). Such ratios of large to small diameters can be 10:1, 15:1, 20:1, 25:1, 30:1, 35:1, 40:1, 45:1, 50:1, 55:1, 60:1, 65:1, 70:1, 75:1, 80:1, 85:1, 90:1, 95:1,100:1. Ratios of large to small diameters can also be greater than 100:1, including ratios of 110:1, 120:1, 130:1,140:1, 150:1,160:1,170:1, 180:1,190:1, and 200:1.

Figure 14:
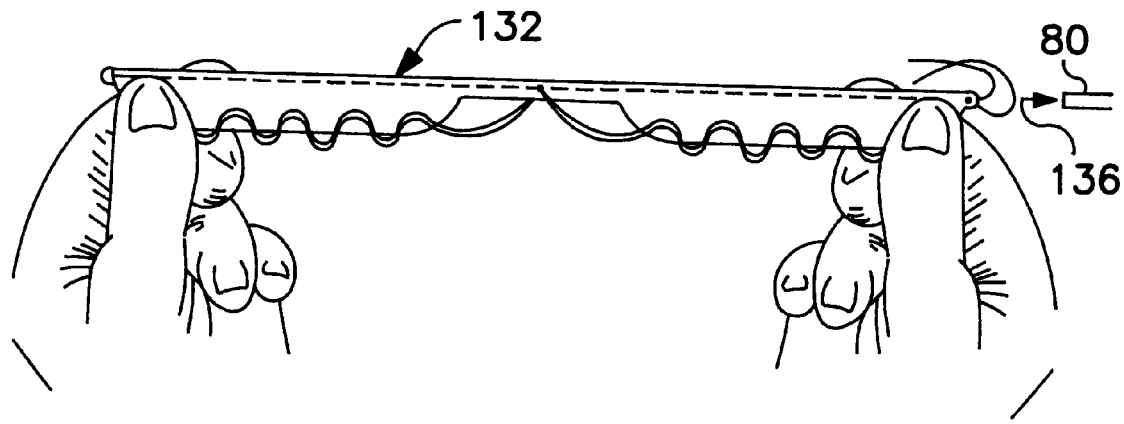
FIG. 14 shows the final device being uncurled and tensioned into a straight profile.

FIG. 14 shows the completed helical closure device 132 being drawn into a linear shape. Once in the linear state, the device can be inserted along the longitudinal axis 136 into a delivery tube 80. Thus the device has a compressed insertion configuration and an enlarged deployed configuration.

Figure 15C:
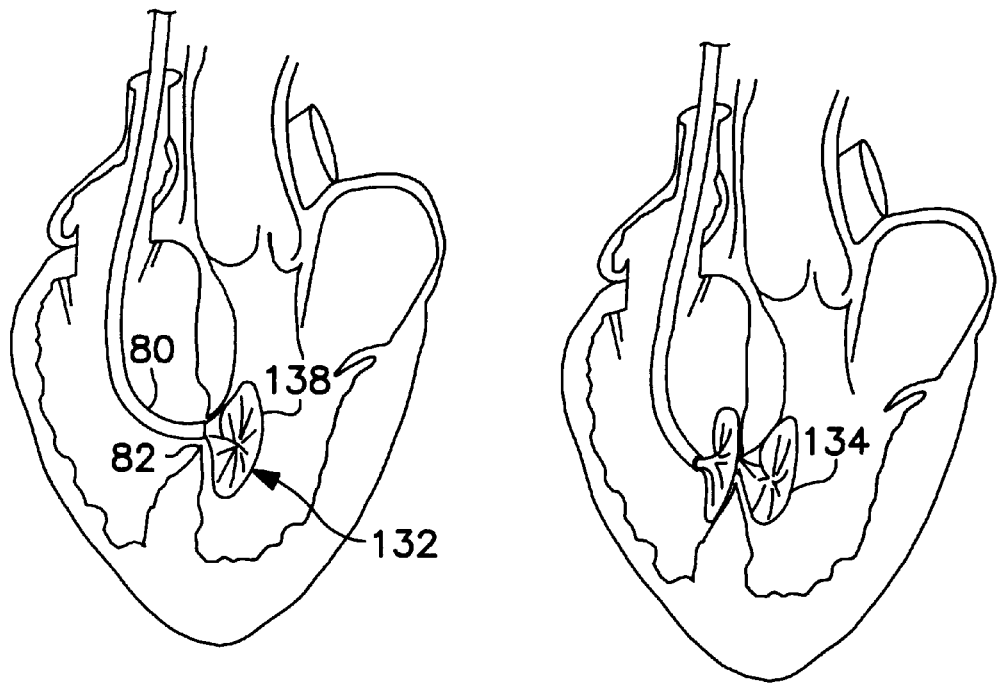
FIGS. 15 (A) through (C) show a helical defect closure device according to the present invention being positioned and deployed in a heart defect.
Figure 15C:
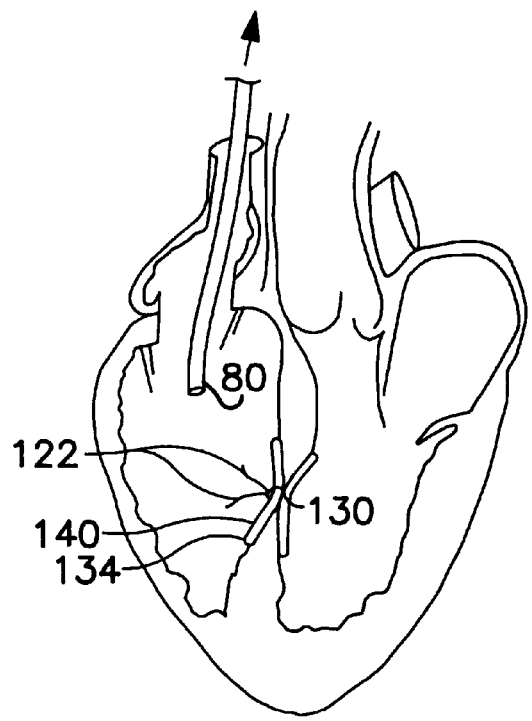

FIGS. 15 (A) through(C) show the deployment of the helical closure device 132. A catheter, or delivery tube 80, is loaded with closure device 132 and deployed in a defect 82. As seen in FIG. 15 (A), the distal side of the helical device 138 expands when released from the catheter 80. As shown in FIG. 15 (B), the distal side of the helical device assumes its memory induced shape 134, which approximates $d_1$ of 76 FIG. 6 (A). As shown in FIG. 15 (C), as the catheter is further withdrawn, the proximal side of the device 140 is deployed. Thus the helical wire acts as an elastic support. This elastic support has a length and is capable of being substantially elongated in the insertion configuration and bending to form an outer periphery of the closure device in the deployed configuration. The suture 122 is then drawn tight, the knot 130 secured and the device assumes its memory induced shape 134. Thus the laminated assembly has a membrane or sealing member comprised of a sheet. This sheet is attached along at least a portion of the length of the helical wire or elastic support in the insertion configuration and this sheet forms a barrier within the formed outer periphery in the deployed configuration.

Figure 16:
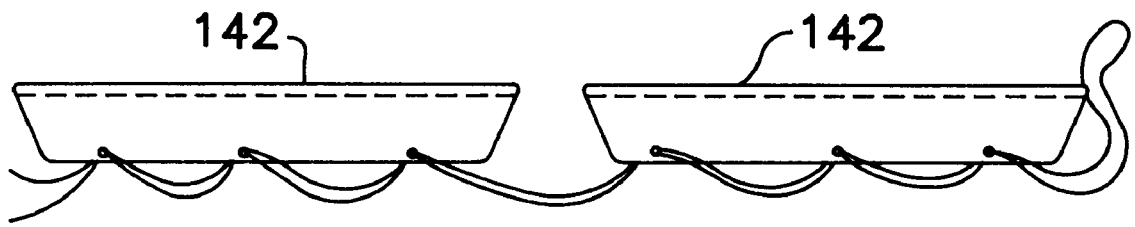
FIG. 16 shows another helical configuration of the present invention with an adjustable grip feature.
Figure 17:
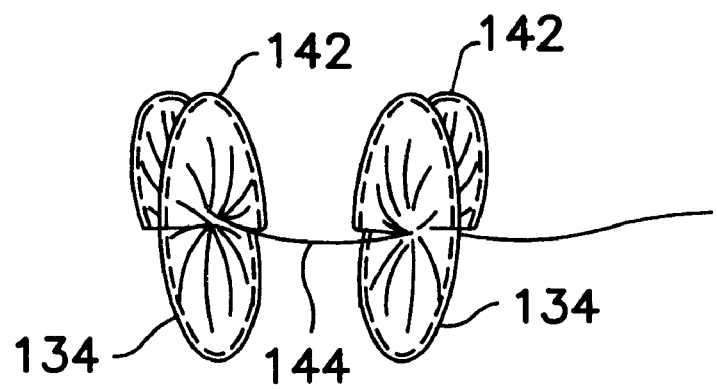
FIG. 17 shows the adjustable grip feature in the deployed or large diameter state.

FIG. 16 shows an alternate helical configuration. The device is fabricated in a process similar to that used for the helical device described above, except the device uses two membrane segments 142, instead of one. The two segments form a relaxed shape 134 as shown in FIG. 17, leaving an adjustable gap 144 between the two membranes 142. This adjustable gap 144 can be used to repair wall defects in a range of wall thicknesses.

Figure 18:
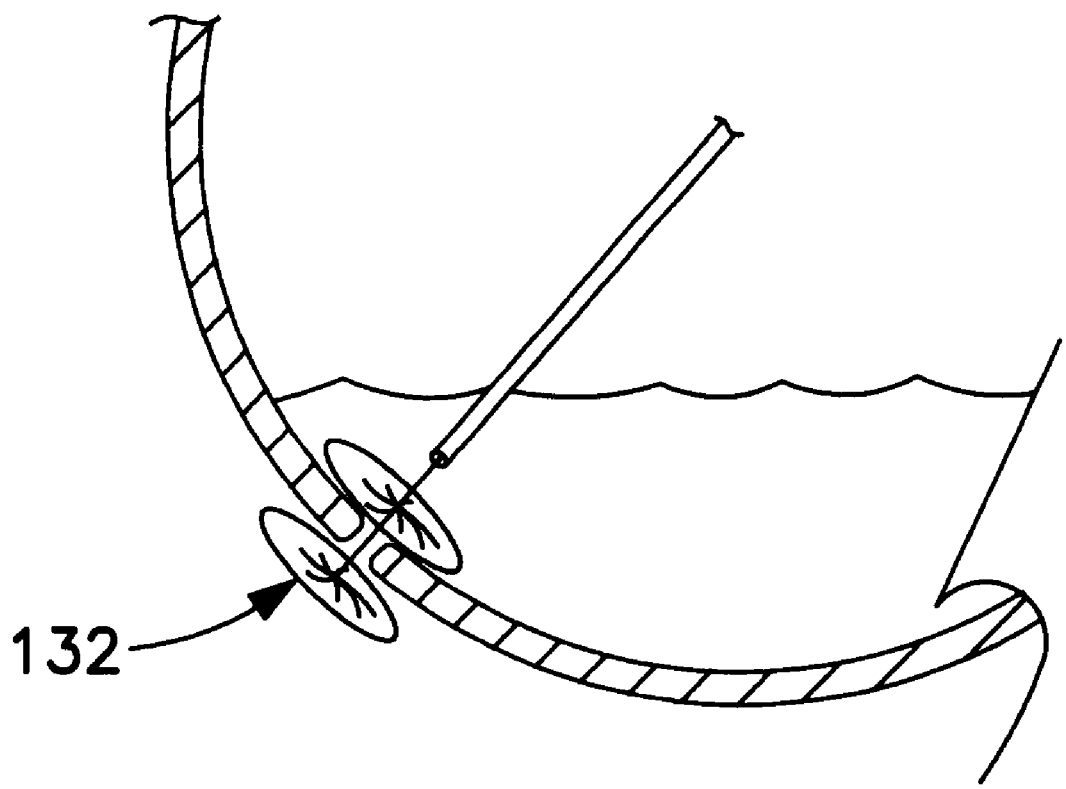
FIG. 18 shows the helical defect closure device positioned in a defect of a container wall.

FIG. 18 shows a vessel wall with a wall defect being sealed by the defect device 132. As seen in FIG. 18, an applicator could be positioned by use of a remote guiding device or be directly employed if conditions allow.

Figure 19A:
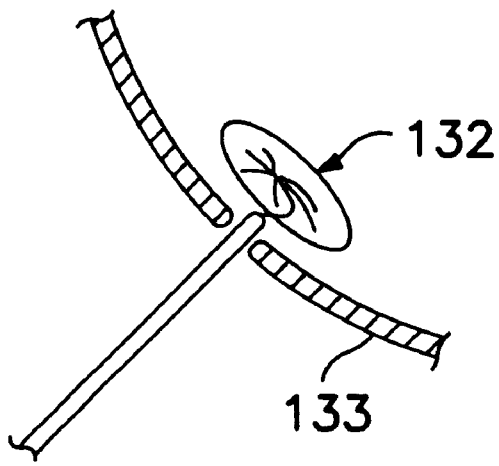
FIGS. 19 (A) through (C) show a helical defect closure device according to the present invention being positioned and deployed in a wall defect.
Figure 19B:
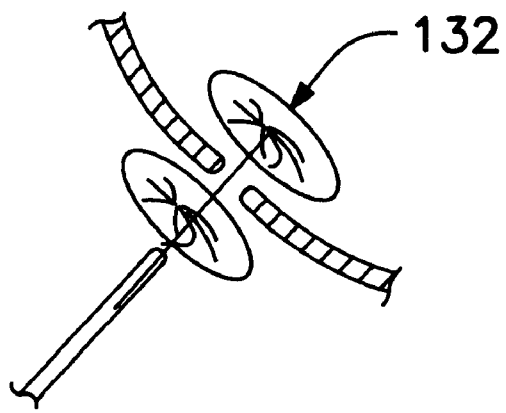
Figure 19C:
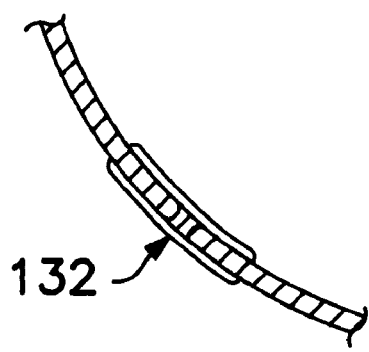

In FIG. 19 (A) through (C), the insertion of the closure device 132 into a wall 133 via an applicator is shown following a procedure similar to that described for FIG. 15 (A) through (C), except a tube is used.

Figure 20:
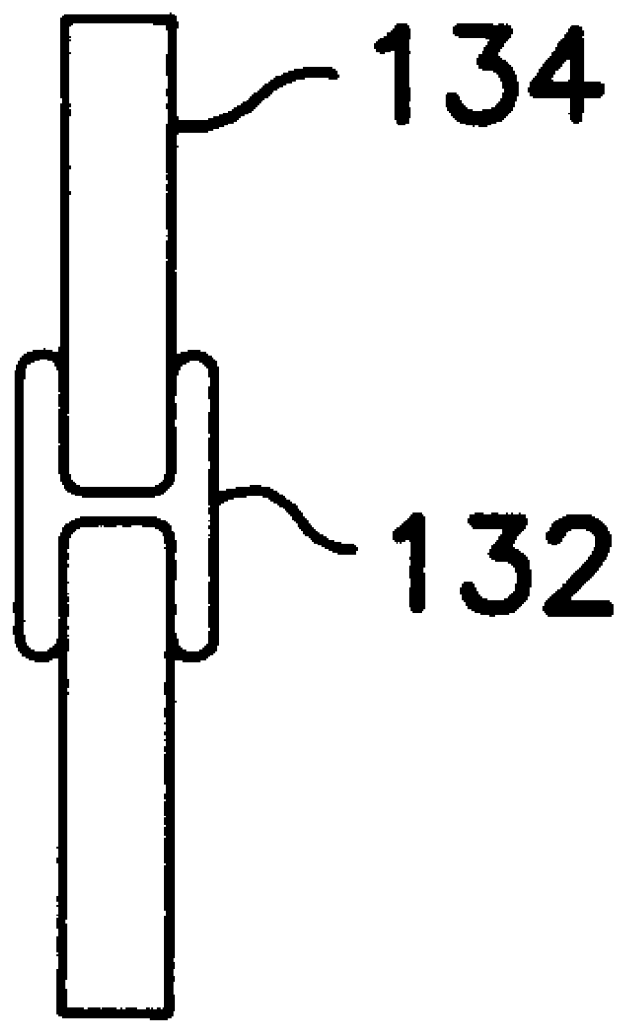
FIG. 20 shows a defect closure device of the present invention in a filter medium.

Although FIG. 18 shows the defect closure device of the present invention being employed in a container wall, defects in filters of any design can be repaired by locating the closure device in a tube and deploying it in the defect of filter wall 134 as shown in FIG. 20 following the procedure of FIGS. 19 (A) through(C).

Another aspect of the present invention is that a seamless support structure can be constructed by machining a thin sheet of material into the shapes, such as those shown in FIGS. 1 and 8 (A) through 8 (F). In one configuration, 0.203 mm thick Ni—Ti alloy is cut into the profile defined in FIGS. 1 and 8 (A) through 8 (F). A second cut removes the inner area of the structure leaving 0.203 mm width of material at the perimeter. The method of manufacturing the seamless part may be by any suitable method, such as Electrostatic Discharge Machining (EDM), laser, photo-etch, die cut, or conventional machining. The resultant part is of square cross-section with corners which can be polished down, such as through electro-polishing or abrasive techniques, to achieve rounded corners.

Another variant of the method by which the seamless support structure can be made is slicing sections off of Ni—Ti tube of 0.203 mm wall thickness and with a perimeter equal that of the shape defined in FIGS. 1 and 8 (A) through 8 (F). The thin ring produced using this technique is polished to remove sharp corners and heat treated into the shapes as shown in FIGS. 1 and 8 (A) through 8 (F) using a heat treating process.

Referring to FIGS. 15 (A) through (C), the distal side 138 of the closure device 132, acts as a distal sealing member and the proximal side acts as a proximal sealing member. These two sealing members can be one continuous segment as shown in FIG. 14. An alternate configuration where the sealing members are made up of two distinct segments is shown in FIGS. 16 and 17. Defect closure devices can also be configured with one, three, four or more sealing members. The sealing member can also act as a partial obstruction to flow through the defect, thus not completely sealing the defect immediately upon deployment.

Figure 21A:
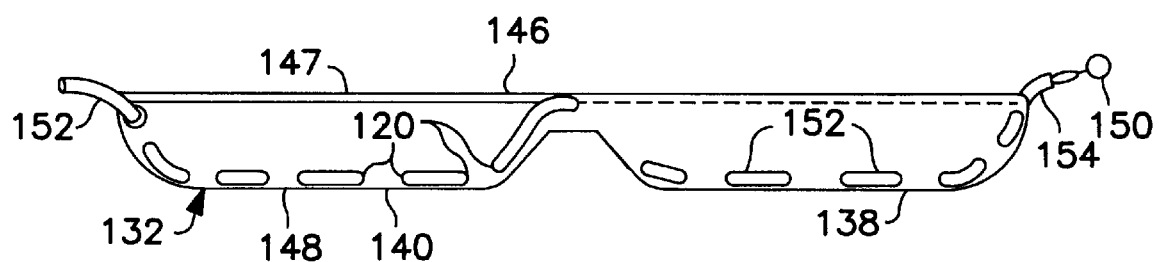
FIGS. 21 (A) and (B) show a latch means for sealing member securing and sealing member to sealing member securing. Also shown is a flexible inner tube sealing member central edge converging means.
Figure 21B:
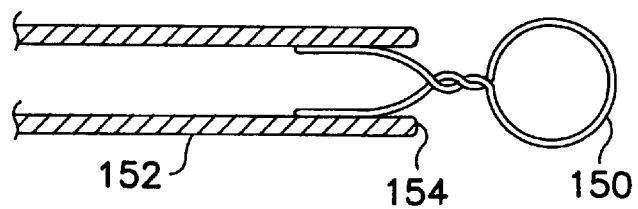
Figure 22A:
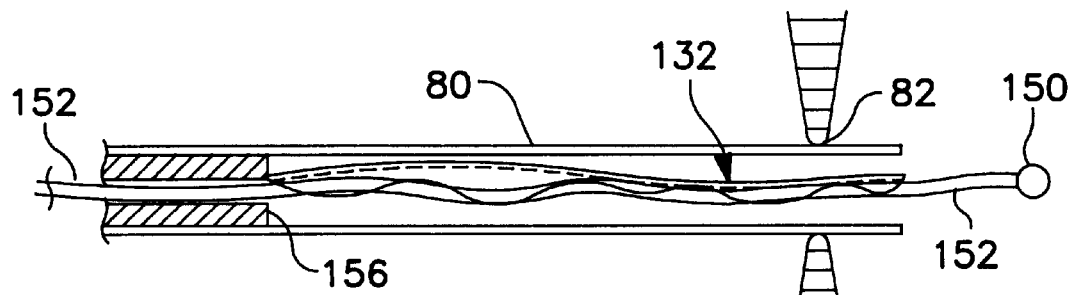
FIGS. 22 (A) through (G) show the delivery and deployment sequence of a helical closure device of the present invention along with a latch means for sealing member securing and sealing member to sealing member securing. Also shown is a flexible inner tube sealing member central edge converging means.
Figure 22B:
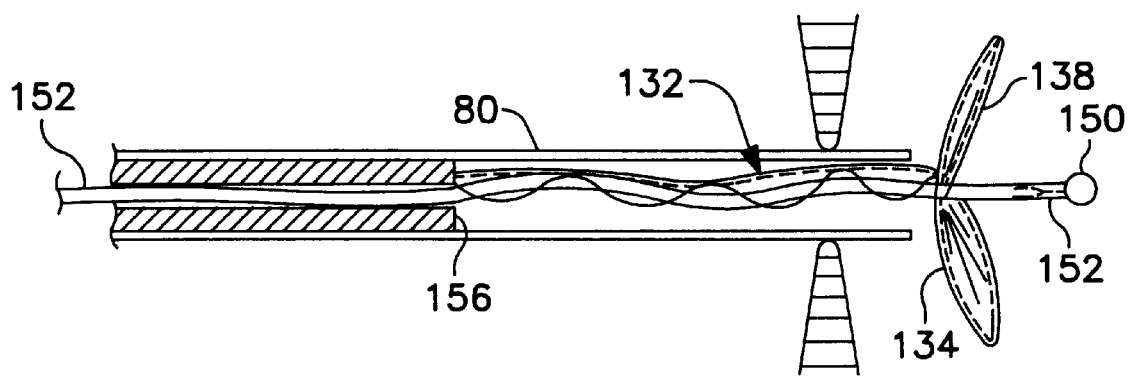
Figure 22C:
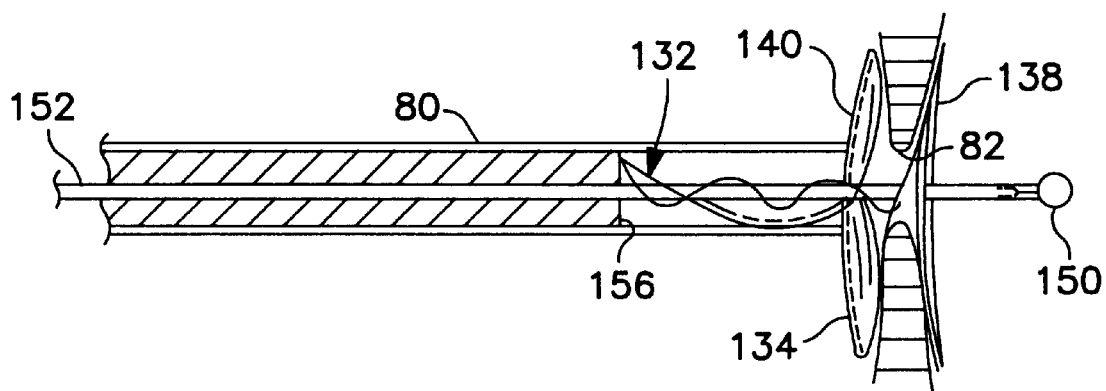
Figure 22D:
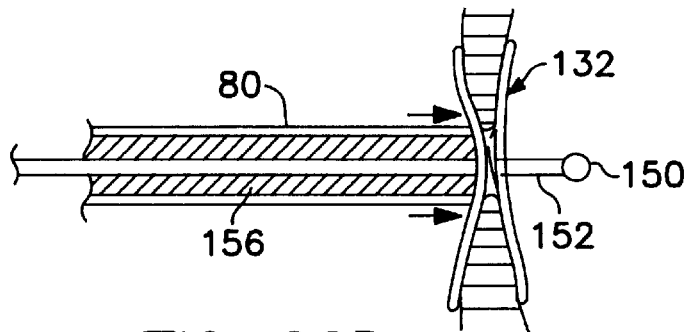
Figure 22E:
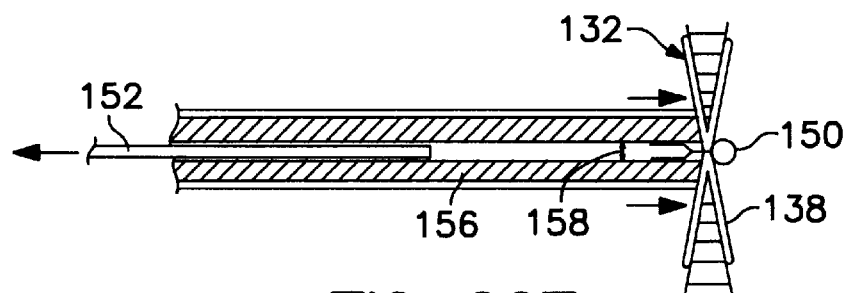
Figure 22F:
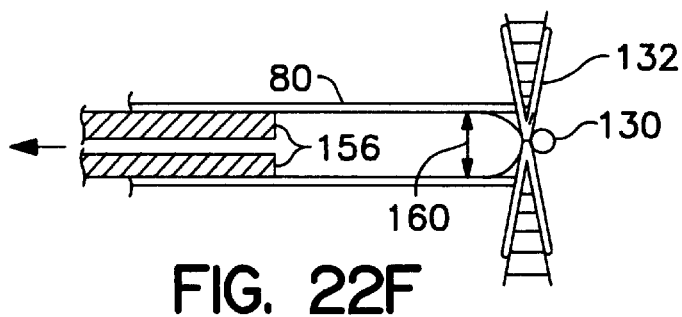
Figure 22G:
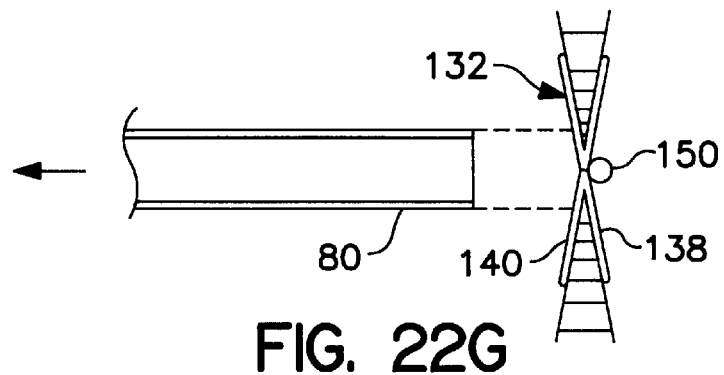

As shown in FIG. 21 (A), a sealing member 147 has a peripheral edge 146 and a central edge 148. As the helical device is deployed the peripheral edge 146 of the sealing member is constrained by the helical wire. To create an obstruction to flow through the defect, or seal the defect, a means must be provided to force the central edge 148 of the sealing member 147 to radially converge in upon itself. Once the central edge 148 of the sealing member is forced to converge radially in upon itself, a means must be provided to secure and maintain the central edge convergence. If more than one sealing member is deployed, a means must be further provided to secure the sealing members together. Sealing member central edge convergence is thus defined as the radial convergence of a sealing member 147 central edge 148, in upon itself thereby creating a seal or obstruction of flow through the defect. Sealing member securing is thus defined as a means to secure and maintain the sealing member edge convergence. Sealing member to sealing member securing is defined as any suitable means to attach sealing members together. Thus the laminated assembly has a membrane or sealing member comprised of a sheet. This sheet is attached along at least a portion of the length of the helical wire or elastic support in the insertion configuration and this sheet forms a barrier within the formed outer periphery in the deployed configuration.

The suture 122 (FIG. 15 (C)) while being tensioned provides a means to force the central edge 148 (FIG. 21 (A)) of the sealing member 147 to radially converge in upon itself, causing an obstruction to flow through the defect. Thus the suture provides a means for sealing member edge convergence. As the suture is tensioned, the precut holes 120 are essentially forced together and become aligned to a common axis, thus forcing the central edge 148 to converge in upon itself. Once the sealing member central edge 148 is converged, the suture knot provides a means for securing the sealing member, thus maintaining the sealing member edge convergence. The suture therefor provides a means for securing the central edge in a converged position. In addition the suture knot provides a means for securing a sealing member to another sealing member. Thus the suture acts as a sealing member edge convergence means, while the suture knot acts as a sealing member securing means and a sealing member to sealing member securing means.

As an alternative to the suture and knot, a wide variety of other securing means can be employed with the present invention. Without limitation, such means may include several other means for providing sealing member edge convergence, sealing member securing and sealing member to sealing member securing have been developed. FIGS. 21 through 24 describe a memory induced latch, sealing member securing means, along with a pre-threaded flexible tube for a sealing member central edge convergence means. As shown in FIG. 21 (A), precut holes 120 in the helical closure device 132 are threaded over a flexible inner tube 152. At the distal end 154, of the inner tube 152, a latch 150 (such as one created from a metal or plastic wire) is captured within the inner tube. FIG. 21 (B) shows the distal end 154 of the flexible inner tube 152 along with the captured latch 150. After deployment of the helical closure device, the latch 150 can be released from the inner tube 152, allowing the latch to spring open into it's relaxed state, thereby providing a sealing member securing means and a sealing member to sealing member securing means. The flexible inner tube 152, over which the precut holes 120 are threaded, acts as the sealing member central edge convergence means.

Deployment of the helical closure device with the latch sealing member securing means and the flexible tube sealing member central edge convergence means is shown in FIGS. 22 (A) through(G). As shown in FIG. 22 (A), the catheter 80 is aligned to and pushed through the defect 82. The catheter 80 contains the helical closure device 132, a device push tube 156, the flexible inner tube 152 and the captured latch 150. The flexible inner tube 152 and captured latch 150 are then advanced out of the catheter as shown in FIG. 22 (A).

As shown in FIG. 22 (B), the pusher tube 156 is then advanced, driving the helical closure device 132 out of the catheter 80. The distal side 138 of the helical closure device 132 then assumes the memory induced shape 134.

As shown in FIG. 22 (C), the catheter 80 is withdrawn away from the defect, forcing the distal side 138 of the closure device 132 against the defect 82. The pusher tube 156 is then advanced toward the defect, driving the helical closure device 132 further out of the catheter 80. The proximal side 140 of the helical closure device 132 then assumes the memory induced shape 134. The pre-threaded flexible inner tube 152 forces the precut holes 120 (FIG. 21 (A)) to become aligned to a common axis and thus provides a sealing member central edge convergence means.

The release of the latch sealing member securing means is accomplished by advancing the catheter 80 and the pusher tube 156 toward the defect, as shown in FIG. 22 (D). As shown in FIG. 22 (E), the flexible inner tube 152 can then be drawn away from the helical closure device 132, seating the latch 150 against the distal side 138 of the helical closure device 132. The precut holes 120 (FIG. 21 (A)) are pre-threaded over the flexible inner tube 152 and are thus aligned to a common axis by the flexible inner tube 152. In this configuration the latch 150 will spring open towards its memory induced shape, and conform the inner diameter 158 of the pusher tube 156.

As shown in FIG. 22 (F), the pusher tube 156 may then be withdrawn away from the helical closure device 132, allowing the latch 150 to further spring open towards the unconstrained memory induced shape and conform to the inner diameter 160 of the catheter 80.

As shown in FIG. 22 (G), the catheter 80 can then be withdrawn from the helical closure device, fully releasing the latch 150, which will then spring open to its memory induced shape. The latch 150 now provides a means to secure the distal side membrane 138 to the proximal side membrane 140 of the helical closure device 132 and also provide a sealing member securing means. Alternate methods for deploying the latch include withdrawing the inner tube 152 and the catheter 80 simultaneously away from the helical closure device 132, or withdrawing the inner tube 152, the pusher tube 156 and the catheter 80 simultaneously away from the helical closure device 132.

As shown in FIG. 23 (A), the latch 150 can be resiliently deformed to conform to the inner diameter 164 of the inner tube 152. As shown in FIG. 23 (B), the latch 150, when released from the inner tube, will spring open to the memory induced shape 162. Alternate latch configurations are shown in FIG. 24.

Figure 25:
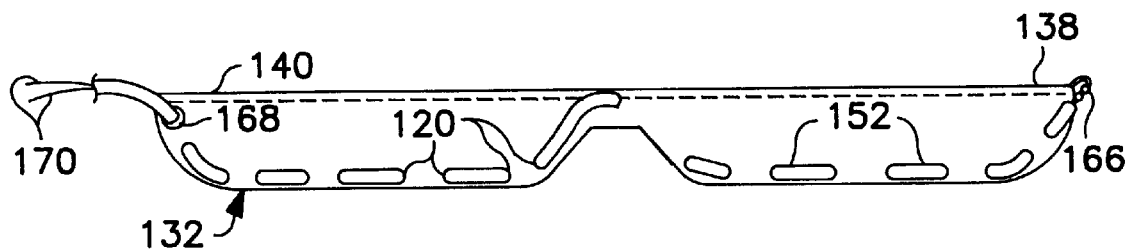
FIGS. 25 and 26 (A) through (D) show a snap and latch means for sealing member securing and sealing member to sealing member securing.
Figure 26A:
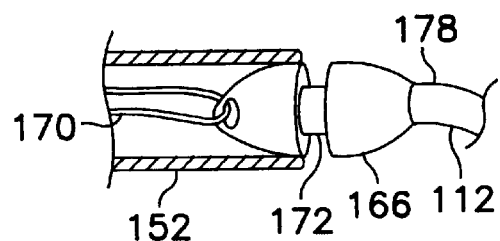
Figure 26B:
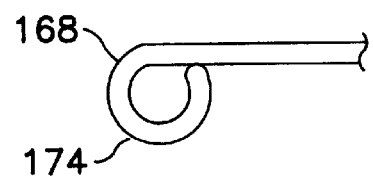
Figure 26D:
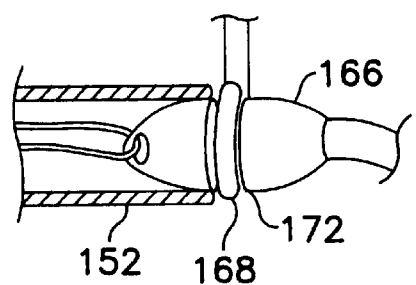
Figure 26C:
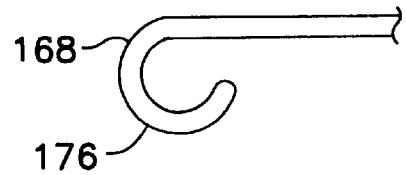
Figure 27A:
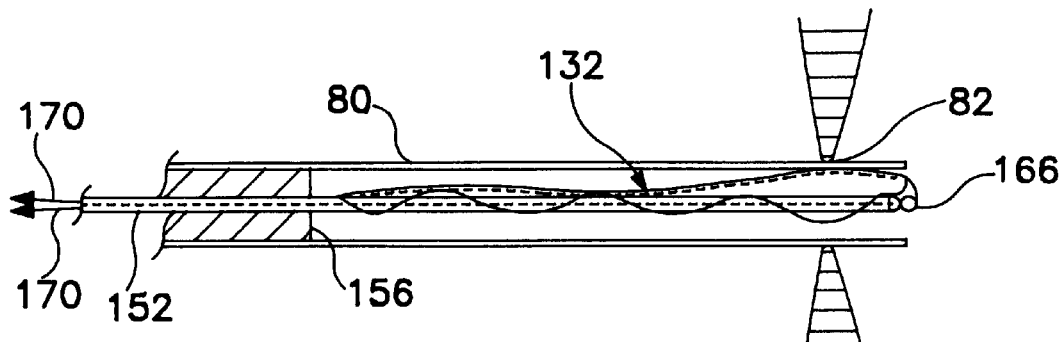
FIGS. 27 (A) through (F) show the delivery and deployment sequence of a helical closure device along with a snap and latch means for sealing member securing and sealing member to sealing member securing. Also shown is a flexible inner tube sealing member central edge converging means.
Figure 27B:
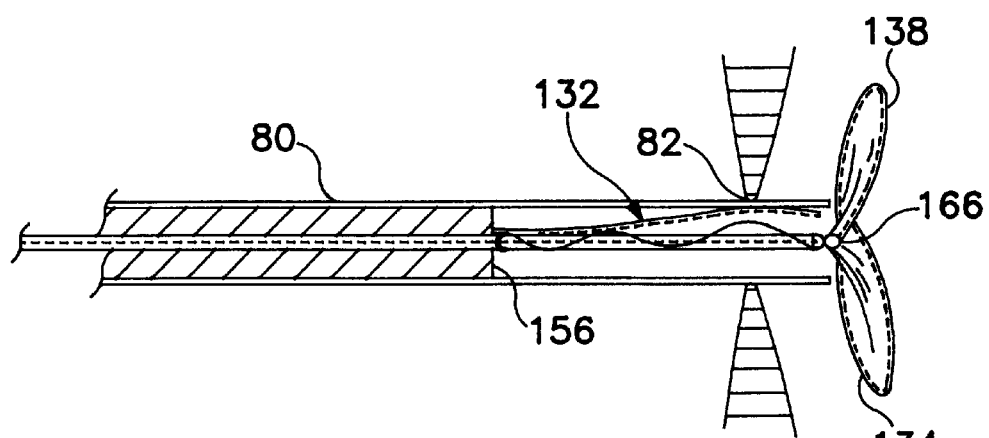
Figure 27C:
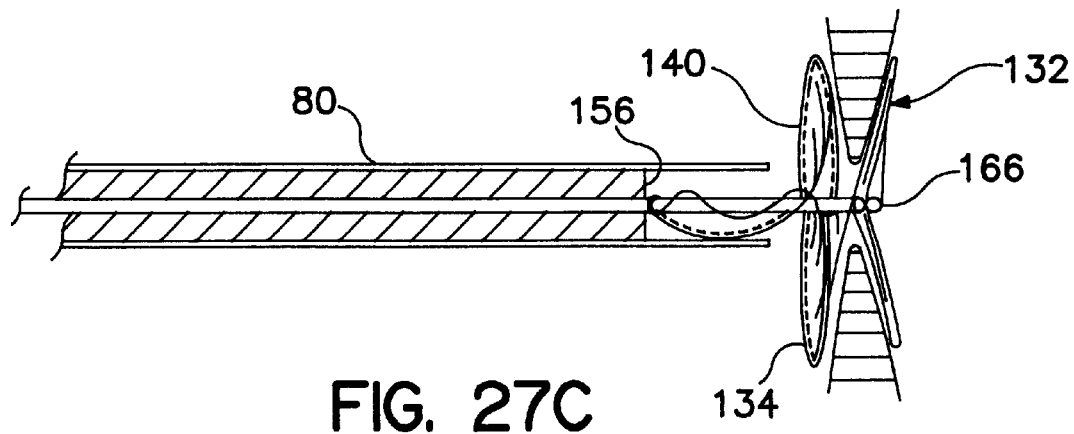
Figure 27D:
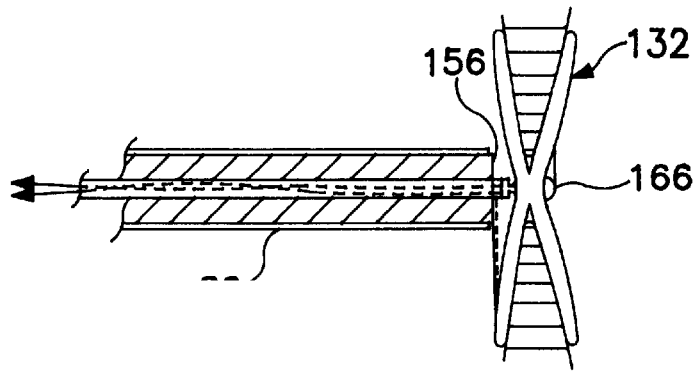
Figure 27E:
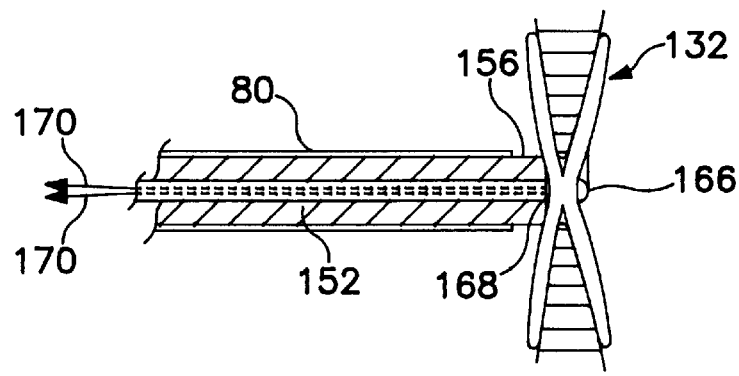
Figure 27F:
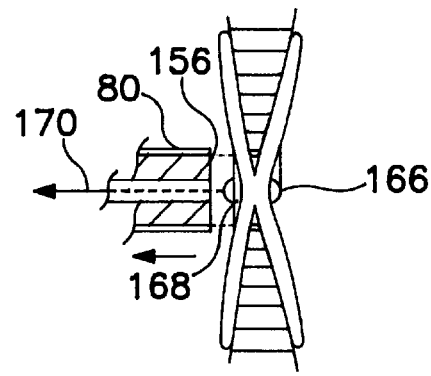
Figure 28A:
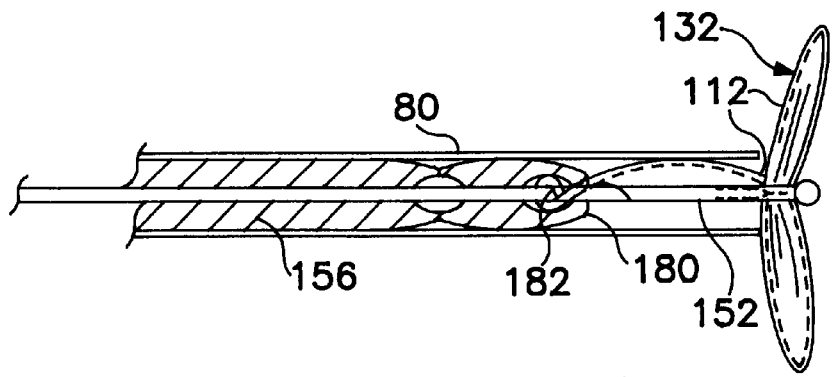
FIGS. 28 (A) through (D) show the deployment sequence incorporating a push tube collet that allows retrieval of a partially deployed helical closure device.
Figure 28B:
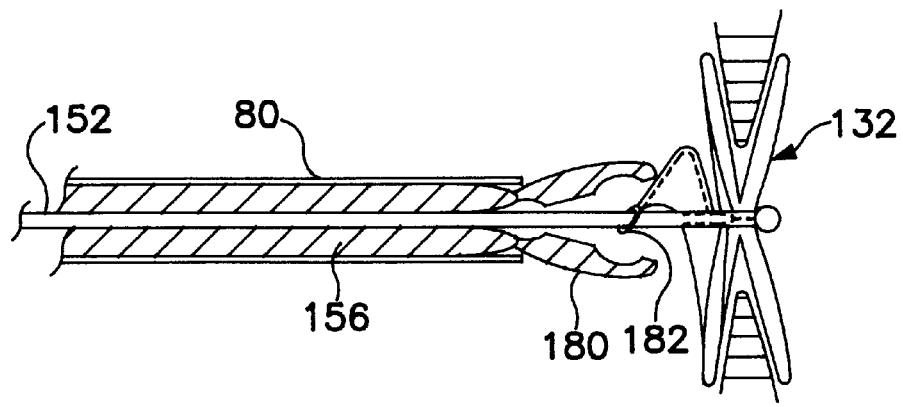
Figure 28C:
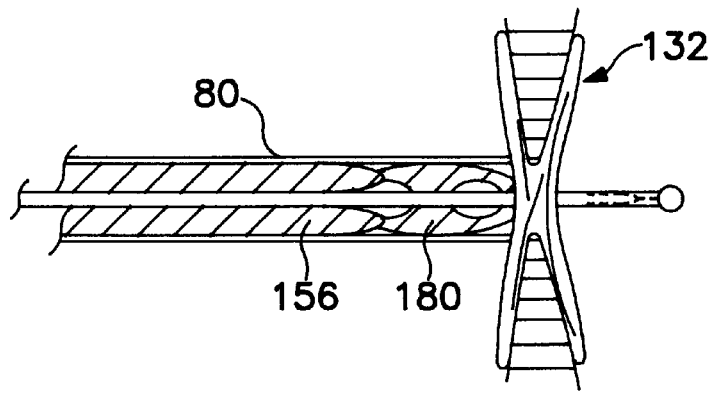
Figure 28D:
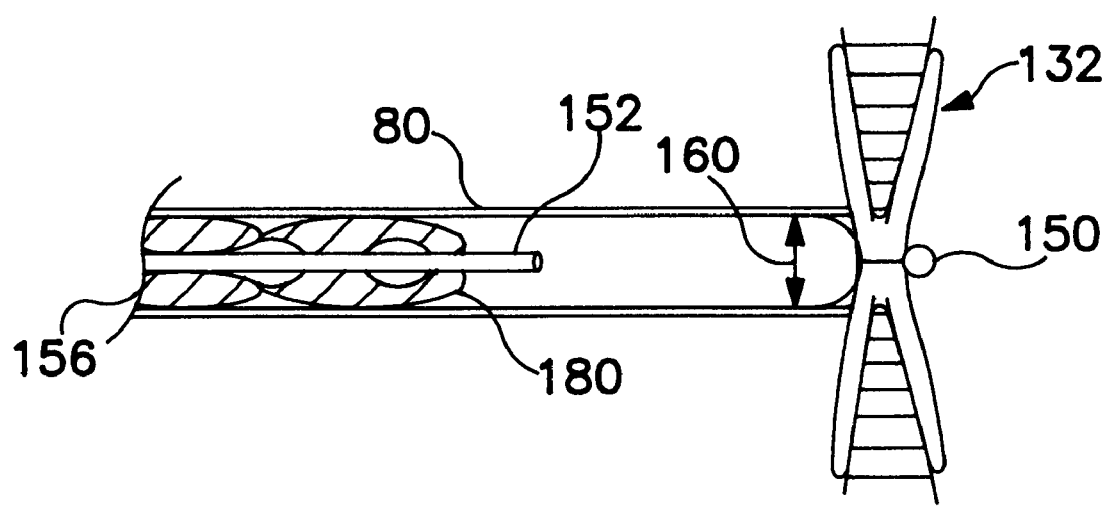

Another alternative to the sealing member central edge convergence and securing means is described in FIGS. 25 through 27. As shown in FIG. 25, the helical closure device 132 has a snap 166 on the distal side 138 and a latch 168 on the proximal side 140. This snap and latch provide the sealing member securing means. The precut holes 120 in the helical closure device 132, are threaded over a flexible inner tube 152. This flexible, pre-threaded inner tube provides the sealing member central edge convergence means.

As shown in FIG. 26 (A), the snap 166 is integrally joined 178 to the helical wire 112 and has a snap groove 166 adapted to receive the latch 168. The snap 172 is also threaded with a pull suture 170 which is threaded through the flexible inner tube 152. The snap 166 is secured to the end of the flexible inner tube 152 by tension on both ends of the pull suture 170.

As shown in FIG. 26 (B), the latch has a memory induced shape 174 and as shown in FIG. 26 (C), the latch 168 is able to be resiliently expanded 176 to a larger diameter.

As shown in FIG. 26 (D), the latch 168 is resiliently expanded over the snap 166 and returns to the memory induced shape, conforming to the snap groove 172, thereby locking the snap 166 into the latch 168.

Deployment of the helical closure device with the snap latch sealing member securing means along with the flexible inner tube sealing member edge convergence means, is shown in FIGS. 27 (A) through(F). As shown in FIG. 27 (A), the catheter 80 is aligned to and advanced through the defect 82. The catheter 80 contains the helical closure device 132, a device push tube 156, the inner tube 152 with the pull suture 170 and the snap 166 secured to the inner tube 152 by tension applied to both ends of the pull suture 170.

As shown in FIG. 27 (B), the pusher tube 156 is then advanced, driving the helical closure device 132 out of the catheter 80. The distal side 138 of the helical closure device 132 then assumes the memory induced shape 134.

As shown in FIG. 27 (C), the catheter 80 is withdrawn away from the defect. The pusher tube 156 is then advanced toward the defect, driving the helical closure device 132 further out of the catheter 80. The proximal side 140 of the helical closure device 132 then assumes the memory induced shape 134. The pre-threaded flexible inner tube forces the precut holes 120 (FIG. 21 (A)) to become aligned to a common axis and thus provides a sealing member central edge convergence means.

As shown in FIG. 27 (D), the push tube is further advanced towards the closure device 132.

As shown in FIG. 27 (E), the push tube contacts the helical closure device 132. The push tube 156 is forced forward against the helical closure device 132, the inner tube 152 is withdrawn while tension is maintained on both ends of the pull suture 170, thereby forcing the snap 166 into the latch 168. The snap 166, once secured by the latch 168, provides the sealing member securing means and the sealing member to sealing member securing means.

As shown in FIG. 27 (F), after the snap 166 is secured by the latch 168, the pull suture 170 can be withdrawn by applying tension to one end. The catheter 80 and push tube 156 can then be withdrawn, completing the defect repair.

As shown in FIGS. 26 (A) through (D), the snap shown 166 can be molded directly onto the helical wire 112, in a secondary operation following the fabrication of the helical device 132 as taught in FIGS. 9 through 12. The snap 166 can be preferably molded from FEP, or from any other suitable bio-compatible polymer. The snap 166 can also be metallic and joined to the helical wire by welding, adhesive bonding, or other joining processes. The latch 168 can be preferably formed from an end of the helical wire 112, by inducing a shape memory. This shape memory forming can be performed by a similar process as described in the forming of the previously described star shaped wire. The latch 168 can also be molded or formed from any suitable biocompatible polymer and be joined directly to the membrane 116 (FIG. 12) or to the helical wire 112.

A means for allowing device retrieval during the deployment is desirable. A device retrieval means is defined as a means to allow the defect closure device to be reinserted into the delivery catheter after partial deployment of the defect closure device. If the closure device is inadvertently mispositioned during deployment, a collet feature, integral to the pusher tube, allows retrieval of the partially deployed device. Thus the device can be withdrawn back into the delivery catheter and redeployed to correct the positioning error. This collet feature is described in FIG. 28 (A). The collet 180 is integrally joined to the pusher tube 156, and is constrained by the catheter 80 so that the collet 180 remains in the closed position. The helical wire 112 of the closure device 132 is formed into an eyelet 182, which is captured by the collet 180. This capturing of the eyelet 182 allows the closure device 132 to be pushed out of the catheter 80 or pulled back into the catheter 80 for retrieval. The preformed eyelet 182 can be replaced by any suitable feature that allows releasable capturing by the push tube 156 retrieval means.

As shown in FIG. 28 (B), the catheter 80 can be withdrawn away from the deployed device 132, allowing the collet 180 to protrude from the catheter 80. The collet is open in the unconstrained state. By removing the mechanical constraint imparted by the catheter 80, the collet 180 is allowed to open, thereby releasing the pre-formed eyelet 182. The closure device 132 is now detached from the push tube 156 and collet 180.

As shown in FIG. 28 (B), the collet 180 and push tube 156 can be completely withdrawn away from the deployed closure device 132. The catheter 80 and collet 180 can then be advanced forward towards the closure device 132, as shown in FIG. 28 (C).

As shown in FIG. 28 (D), the inner tube 152 can be withdrawn away from the closure device 132, allowing the latch 150 to spring open towards the unconstrained memory induced shape and conform to the inner diameter 160 of the catheter 80. The catheter 80 can then be withdrawn away from the closure device, completing the deployment as shown in FIG. 22 (G).

Figure 29A:
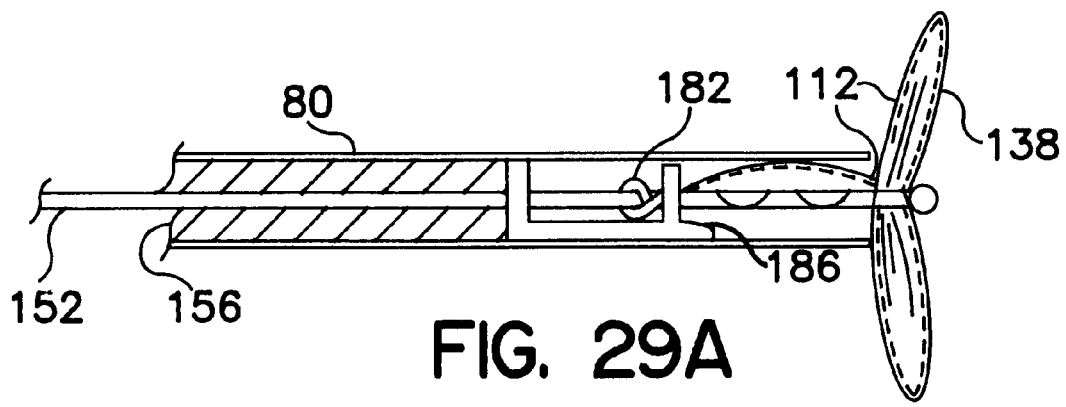
FIGS. 29 (A) through (C) show a retrieval lock design.
Figure 29B:
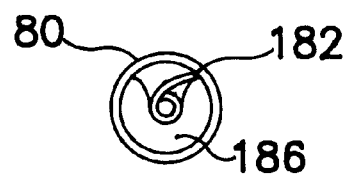
Figure 29C:
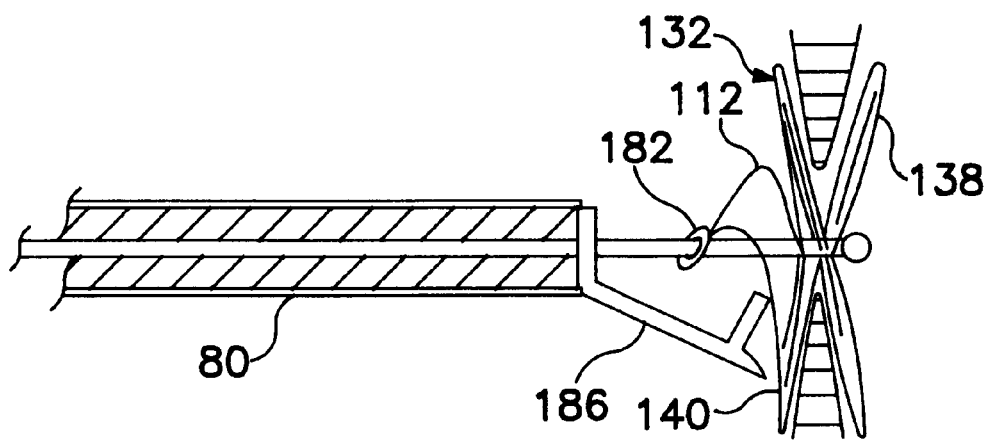

FIGS. 29 (A) through (C) show an alternate device retrieval means. As shown in FIG. 29 (A), the push tube has a retrieval lock 186 integral to the push tube 156. The retrieval lock 186 captures the eyelet 182 formed onto the helical wire. FIG. 29 (B) shows an end view of the retrieval lock 186 with the eyelet 182 in the captured state. As shown in FIG. 29 (C), the retrieval lock 186 springs open in the unconstrained state, releasing the eyelet 182. The retrieval lock 186 allows the closure device 132 to be pulled back into the delivery catheter 80 if re-deployment is necessary. The closure device 132 deployment is completed in the sequence described in FIGS. 28 (A) through (D).

Figure 30A:
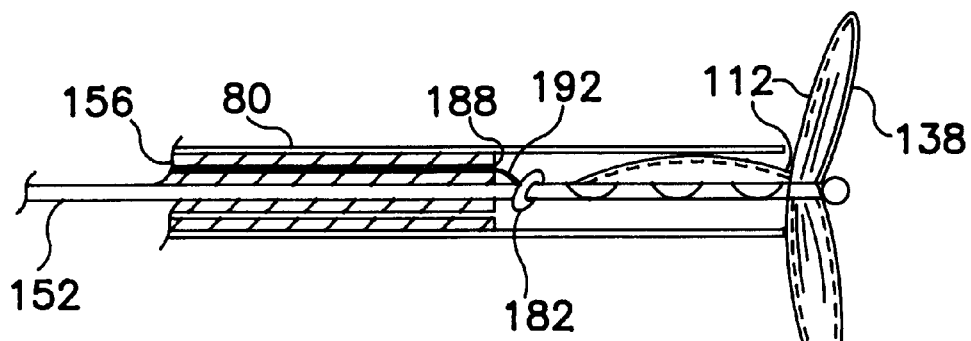
FIGS. 30 (A) through (C) show a suture retrieval means.
Figure 30B:
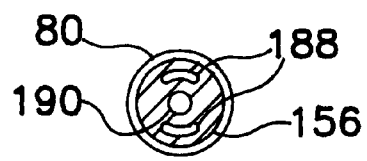
Figure 30C:
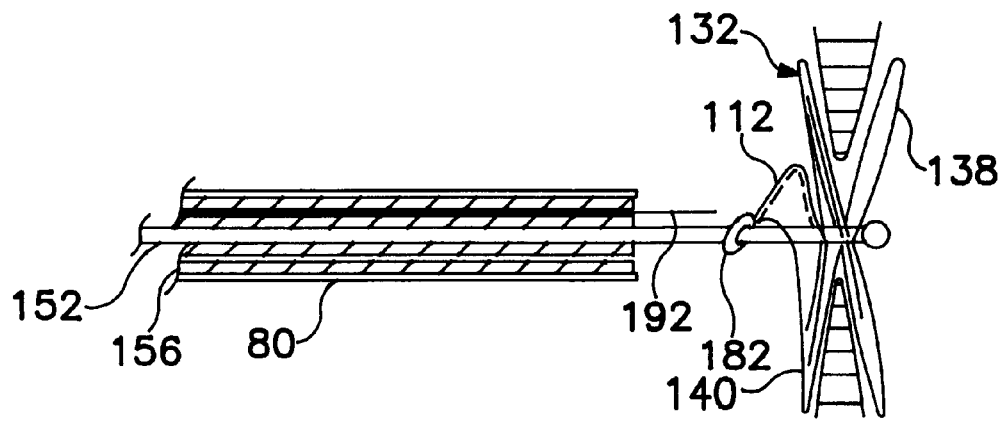

FIGS. 30 (A) through (C) show a suture retrieval means. As shown in FIG. 30 (A), a suture 192 is pre-threaded through the eyelet 182. By tensioning both ends of the suture, the closure device can be drawn back into the delivery catheter 80 if re-deployment is required. As shown in FIG. 30 (B), the push tube 156 has single or multiple suture lumens 188, in addition to the inner tube lumen 190 as shown in FIG. 30 (C). Deployment of the closure device 132 can be completed by tensioning one end of the retrieval suture 192, thereby unthreading and releasing the suture from the eyelet 182. The closure device 132 deployment is completed in the sequence described in FIGS. 28 (A) through (D).

Figure 31A:
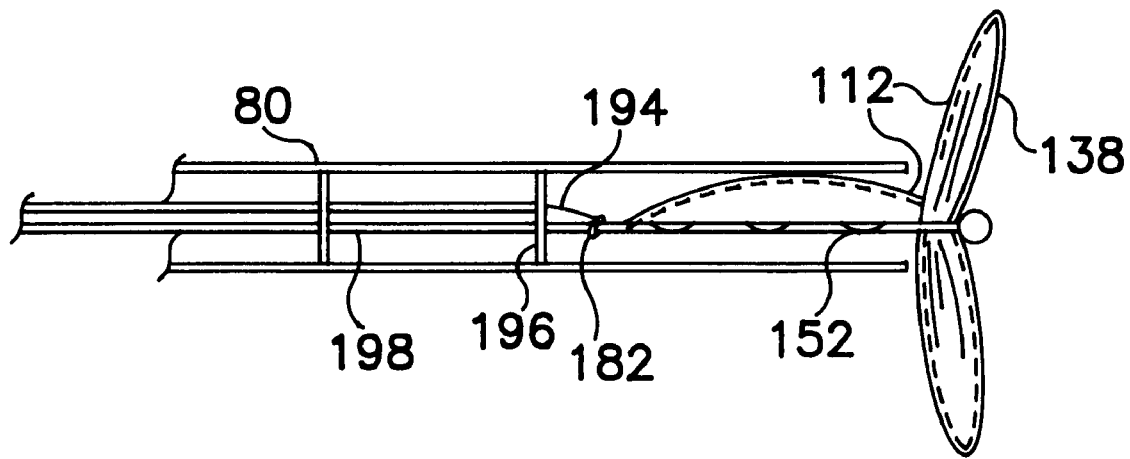
FIGS. 31 (A) and (B) show a wire snare retrieval design.
Figure 31B:
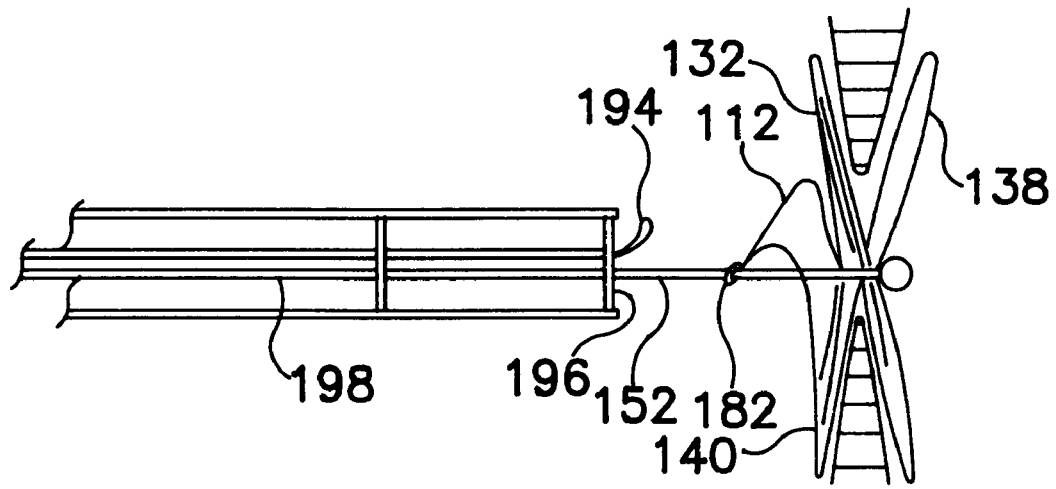

FIGS. 31 (A) and (B) show a snare retrieval means. As shown in FIG. 31 (A), the pusher tube has been replaced by a two lumen tube or double tube 198 configuration. One tube or lumen constrains the inner tube 152, while the second tube or lumen contains a wire snare 194. The wire snare 194 is hooked over the end of the eyelet 182. When the snare 194 is tensioned, the eyelet 182 is pulled back against the pusher piston 196. Thus if the pusher piston 196 and the snare 194 are retracted together away from the defect site, the closure device will be retrieved and drawn back into the delivery catheter 80. The closure device is ejected from the delivery catheter 80 by advancing both the pusher piston 196 and the snare 194. As shown in FIG. 31 (B), the eyelet 182 can be released by advancing the snare 194 relative to the pusher piston 196. The closure device 132 deployment is completed in the sequence described in FIGS. 28 (A) through (D).

Figure 32A:
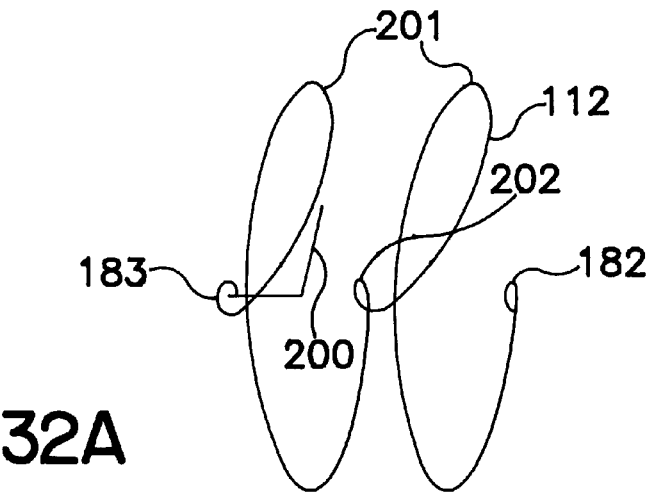
FIGS. 32 (A) through (C) show a closure device with a integral eyelet and latch.
Figure 32B:
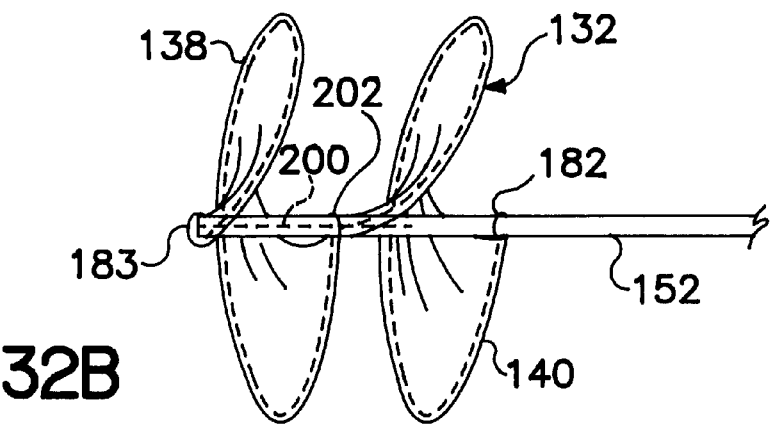
Figure 32C:
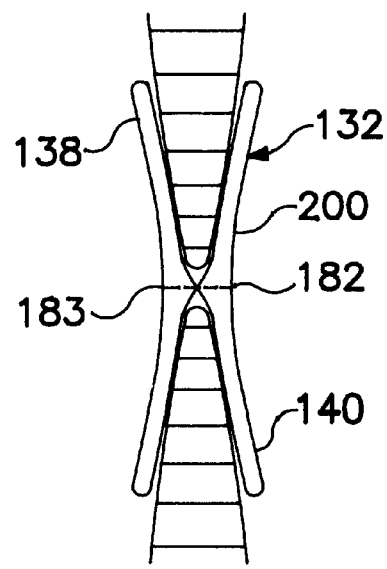
Figure 34:
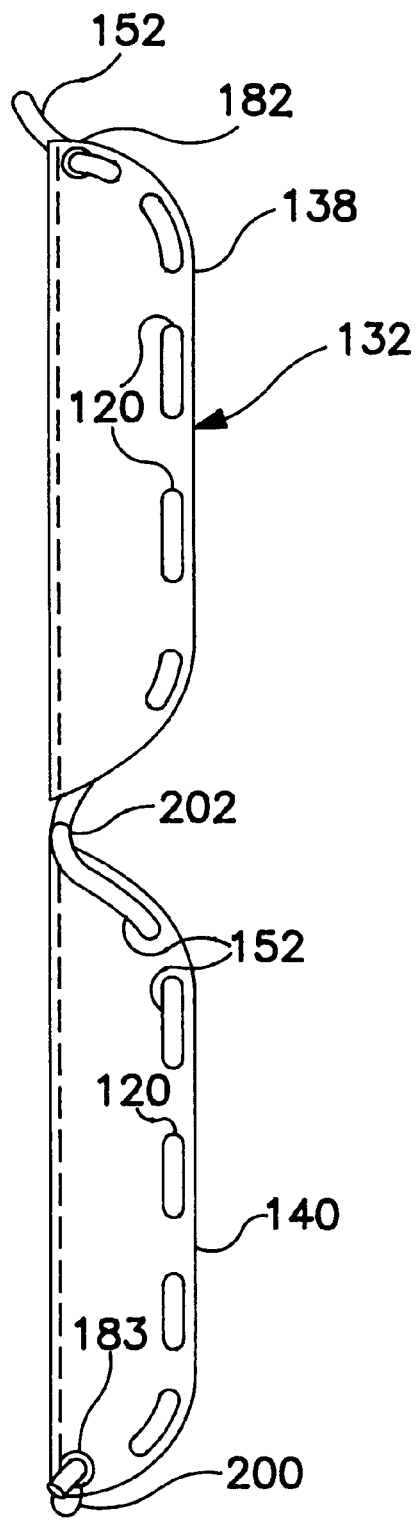
FIG. 34 shows a closure device with two separate sealing members.

Alternative closure device configuration is shown in FIG. 32 (A) through (C) and FIG. 34. This configuration incorporates a inner tube for the sealing member edge convergence means, and an integral eyelet and latch for the sealing member securing and sealing member to sealing member securing means. As shown in FIG. 32 (A), the helical wire 112 is formed into two loops or peripheries 201, a proximal eyelet 182, an intermediate eyelet 202, a distal eyelet 183 and a latch 200. A bias may be applied to the wire to encourage the deployment rotational direction and the longitudinal deployment direction in order to assure a specific deployed configuration. As shown in FIG. 32 (B), the inner tube 152 is threaded through the three eyelets 182, 202, 183 and the latch 200 is then inserted into the inner tube 152. As shown in FIG. 34, the inner tube 152 is also threaded through the pre cut holes 120 in the sealing members 138 and 140. The inner tube 152 threading through the precut holes 120 is not shown in FIG. 32 (B) for clarity. This configuration is deployed in the sequence described in FIGS. 22 (A) through (G). Referring to FIGS. 23 (B) and 32 (A), the latch 150 and memory induced shape 162 have been replaced with the distal eyelet 183 and latch 200 respectively. Thus the sealing member securing and sealing member to sealing member securing means have been integrated into the helically formed wire. As shown in FIGS. 32 (B) and (C), the latch 200 passes through the three eyelets 182, 202, 183 and springs open to the unconstrained state when the inner tube 152 is withdrawn. The latch 200 thus acts as a sealing member securing and sealing member to sealing member securing means. The latch 200 can be formed into alternate shapes such as loops, coils and peripheries. Multiple latches can also be configured. Closure devices with single or multiple sealing members can also be configured.

The closure device configuration shown in FIGS. 32 (A) through (C) and FIG. 34, comprises two loops or peripheries 201, approximating diameters ranging from 0.10" to 10" (2.54 mm to 254 mm), with a preferred approximate diameter range of 0.25" to 2.0" (6.35 mm to 50.8 mm), with a most preferred approximate diameter range of 0.75" to 1.25" (19.05 mm to 31.75 mm). The three eyelets 182, 202 and 183 are formed to approximate diameters ranging from 0.008" to 0.60" (0.20 mm to 15.2 mm), with a preferred approximate diameter range of 0.015" to 0.050" (0.38 mm to 1.27 mm), with a most preferred approximate diameter range of 0.035" to 0.045" (0.89 mm to 1.14 mm). Various sizes of closure devices can be configured to adapt to any specific size of a defect, ranging from 0.10" (2.54 mm) or less in diameter to larger than 10" (254 mm). The three eyelets 182, 202 and 183 are preferably spaced 5.0" (127 mm) apart, allowing the closure device to span a range of defect wall thicknesses ranging from 0.010" to 0.50" (0.25 mm to 12.7 mm). This eyelet spacing can be configured to adapt to various defect wall thickness, ranging from less than 0.10" (2.54 mm) to greater than 10" (254 mm). The helical wire or elastic support can have a diameter range of 0.0005" to 0.250" (0.013 mm to 6.35 mm), with a preferred range of 0.004" to 0.040" (0.10 mm to 1.02 mm), with a most preferred range of 0.008" to 0.012" (0.20 mm to 0.30 mm). The flexible inner tube can have inner diameters ranging from 0.005" to 0.300" (0.13 mm to 7.62 mm), with a preferred range of 0.010" to 0.030" (0.25 mm to 0.76 mm), with a most preferred range of 0.018" to 0.024" (0.46 mm to 0.61 mm). The flexible inner tube can have an outer diameter ranging from 0.007" to 0.500" (0.18 mm to 12.7 mm), with a preferred range of 0.014" to 0.040" (0.36 mm to 1.02 mm) and a most preferred range of 0.023" to 0.029" (0.58 mm to 0.74 mm). The flexible inner tube can be fabricated from any suitable bio-compatible material including polymers or metals. The helical wire or elastic support can be fabricated from any material having the required degree of resiliency. A preferred flexible inner tube and helical wire material is Nitinol, procured from Fort Wayne Metals Research, Fort Wayne, Ind. The flexible inner tube and the helical wire can be surface treated or coated to enhance the material's bio-compatibility.

The following paragraphs describe a preferred method of manufacturing the helical closure device. The wire is initially cut to a 18 inch length and wound onto a helical jig that constrains the wire in a preferred form, including the peripheries, eyelets and latch. The wire is then oven tempered at 450° for 20 minutes. The wire is then quenched in room temperature water and removed from the helical jig. The formed wire is then tensioned to a linear form and wrapped with an FEP film. The FEP film is 0.060" to 0.085" (1.52 mm to 2.16 mm) wide, 0.0005" to 0.001" (0.013 mm to 0.025 mm) thick and can be procured from Norton Performance Plastics Corporation, Wayne, N.J. The film can be wrapped onto the wire by use of commercially available winding equipment or wrapped by hand. The FEP or other suitable bonding material can also be sprayed, coextruded or procured in tube form and slid over the wire. The wire is then removed from the tensioning device, hung vertically in an oven and air heated at 300° for 1.5 minutes. To produce a void free coating, the wire should be supported to avoid wire to wire or wire to oven contact.

The sealing member or membrane is formed from a lamination of expanded PTFE film. Eight films of expanded PTFE are layered onto a vacuum chuck, each film rotated about 90 degrees relative to each other. A high temperature tube is then placed across the center of the layered expanded PTFE film, with both ends of the tube extending beyond the layered film. The layered expanded PTFE film is then folded over the high temperature tube. The assembly is then sintered with the film edges constrained and vacuum applied to the chuck, at 370° for approximately 15 minutes. The laminated assembly is then placed onto a laser and a sealing member outline is cut along with the holes for threading the inner tube. This process is repeated to form a second sealing member with a second high temperature tube. The previously coated, helically formed wire is inserted into the two high temperature tubes and the high temperature tubes are then removed from the laminated assembly. The device is then constrained into a linear form and temporary sutures are threaded through the precut holes in the sealing members. These temporary sutures are then tensioned causing the central edges of the seal members to radially converge in upon themselves, thus assuming the final deployed configuration. The device is then air heated at 330° for 5 minutes causing the FEP coating on the wire to bond to the expanded PTFE laminate. The device is cooled, the temporary sutures removed and the seal members and formed eyelets are threaded onto a flexible inner tube. Excess wire is then removed and the latch is inserted into the flexible inner tube. The device is then loaded into the delivery catheter.

Figure 33A:
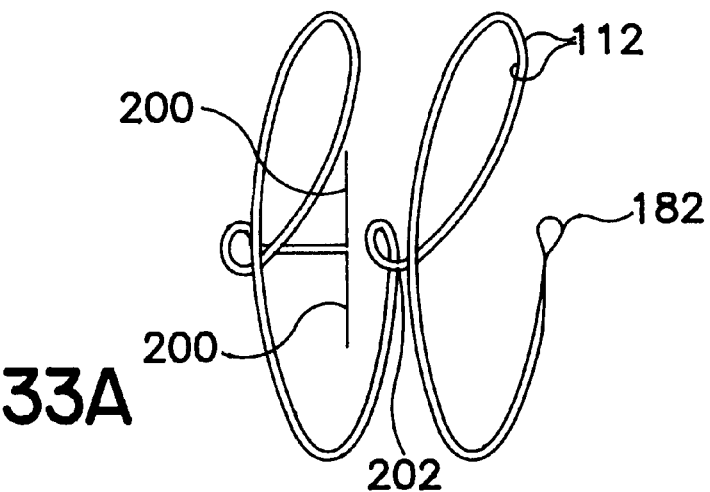
FIGS. 33 (A) through (C) show a double wire device.
Figure 33B:
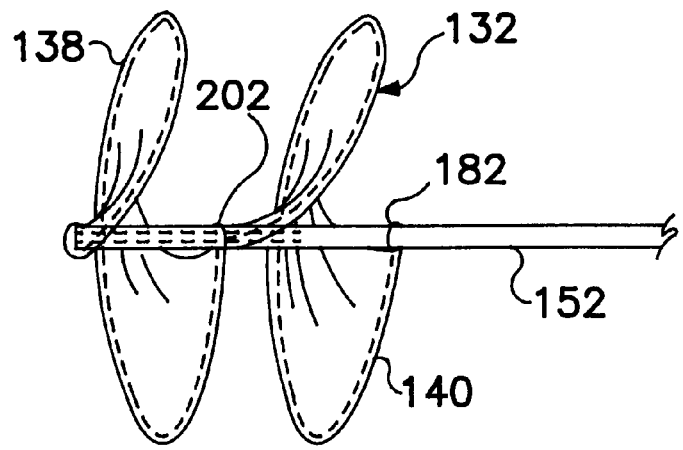
Figure 33C:
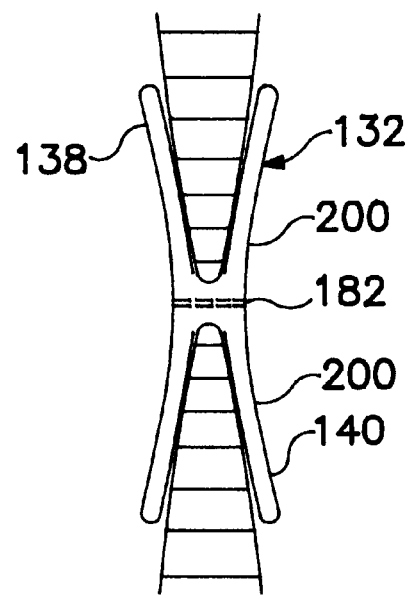

Shown in FIGS. 33 (A) through (C) is an alternate closure device design, incorporating a double helical wire or elastic support. In this configuration a single wire is formed into the double wire shown in FIG. 33 (A). This configuration allows the use of a smaller diameter wire and also facilitates the eyelet 182 formation and readily forms two latches 200.

Multiple wires can be formed to this configuration including but not limited to two, three, four, five, six or more wires.

As shown in FIG. 34, the sealing members 138 and 140 can be distinct members. Single or multiple sealing members can be configured including but not limited to one, two, three, four, five, six or more sealing members.

FIG. 35 (A) and (B) show guide wire features 206 and 208 integral to the delivery catheter 80. These configurations reduce the insertion force and friction between the guide wire 204 and the delivery catheter 80. In addition the outer diameter of the catheter 80 is reduced along a substantial portion of the catheter length. In addition these configurations allow the catheter to be positioned into the defect using traditional "over the wire" technology.

Figure 36:
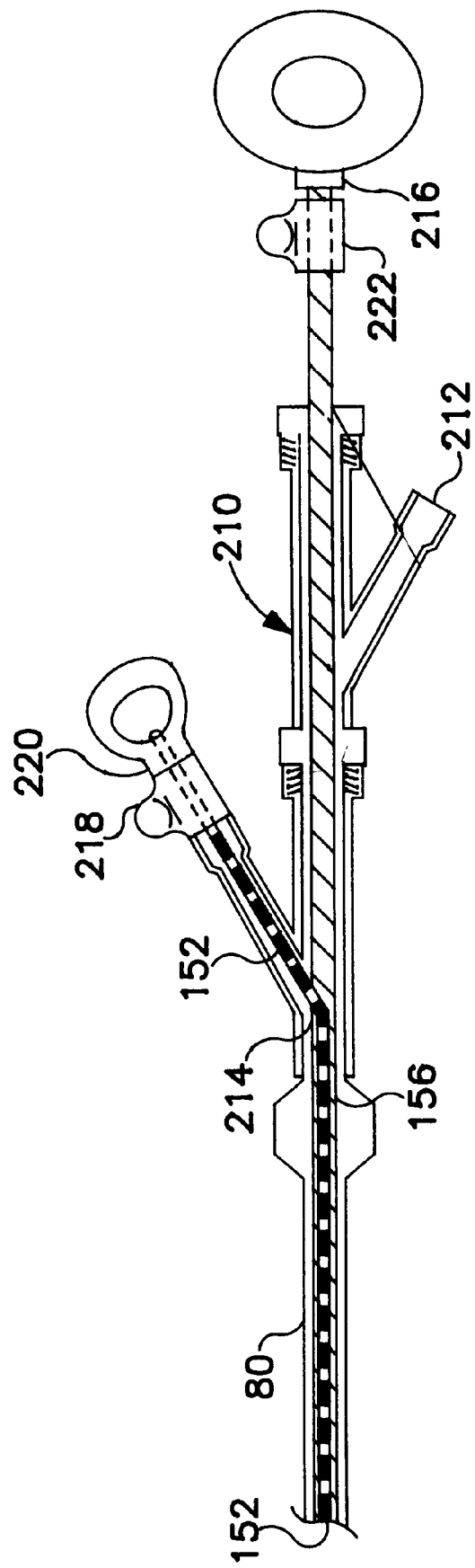
FIG. 36 shows the components relating to the proximal or external end of the catheter assembly for use with the present invention.

The components of the proximal or external end of the delivery system 210 are shown in FIG. 36. A syringe port 212 is provided for flushing and deairing of the catheter system prior to device deployment. The pusher tube 156 exits the proximal end of the catheter assembly 210. Attached to the exposed pusher tube 156 is a removable safety collar 222 and a fixed stop collar 216. The fixed stop 216, when seated against the removable stop 222 limits the pusher tube 156 advancement to the approximate 95% deployed stage. Thus at this 95% deployed stage, the closure device 132 is still captured by and the push tube collet 180 (Refer to FIG. 28 (A)) being over the pre-formed eyelet 182. To release the closure device 132, the removable stop 222 is removed, the pusher tube 156 is fully advanced allowing the collet 180 to open and release the closure device.

The flexible inner tube 152 exits the proximal end of the catheter assembly 210 through a separate port. To allow independent advancement of the pusher tube 156 and the inner tube 152, the inner tube 152 passes through a slit 214 in the wall of the pusher tube 156. Attached to the exposed inner tube 152, is a fixed stop collar 220 and a removable collar 218. When the stop collar 220 is seated against the removable collar 218, the inner tube 152 is contained and protected within the distal end of the catheter 80 and in addition, accidental device deployment is safeguarded. After the catheter 80 is properly positioned relative to the defect, the removable collar 218 is removed and the inner tube 152 is fully advanced to protrude out of the catheter 80, to a position as shown in FIG. 22 (A) or 28 (A). Although the latch membrane to membrane securing means has been shown, the same deployment procedure described in FIGS. 28 and 29 are applicable to the snap and latch securing means described in FIGS. 25 through 27 and to the integral eyelet and latch design shown in FIGS. 32 and 33.

Figure 37A:
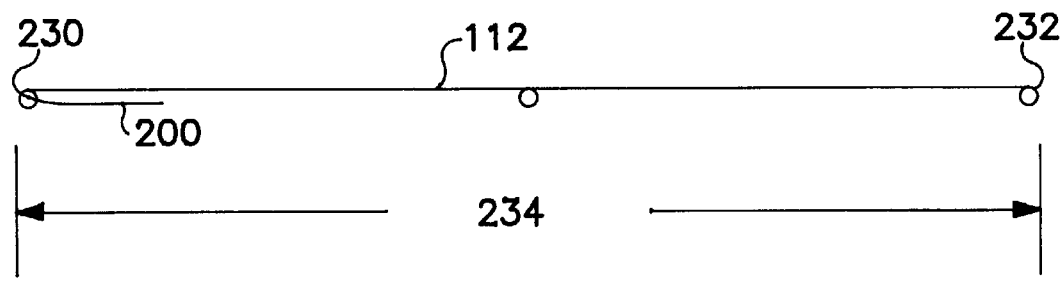
FIGS. 37 (A) through (C) show the closure device in the elongated delivery state along with the deployed lengths across varying defects.
Figure 37B:
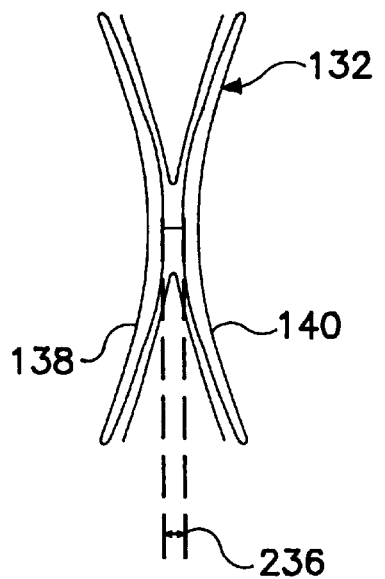
Figure 37C:
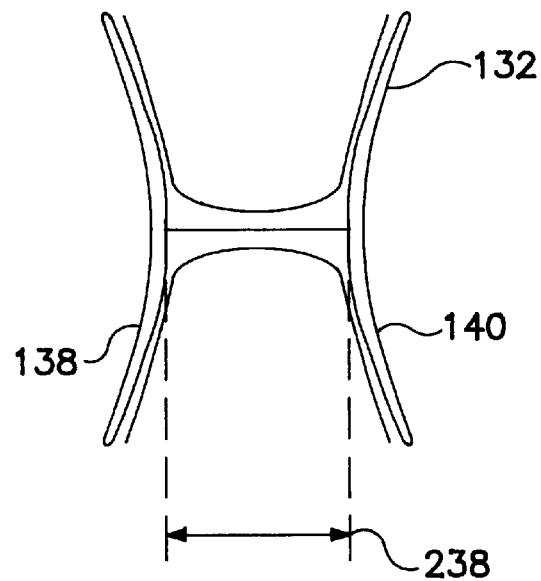
Figure 38A:
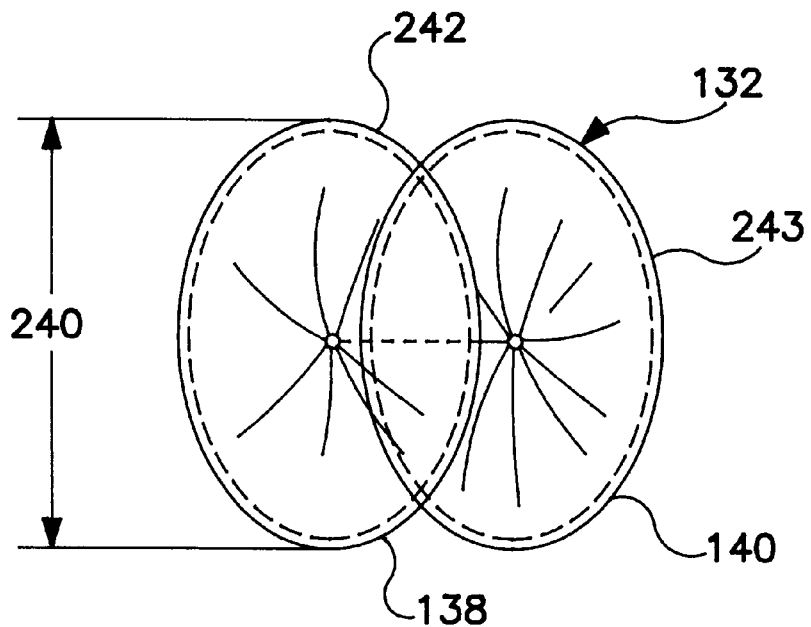
FIGS. 38 (A) and (B) show formed outer peripheries having linear lengths.
Figure 38B:
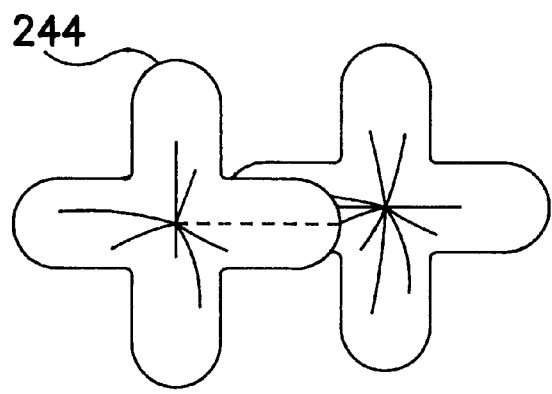
Figure 39A:
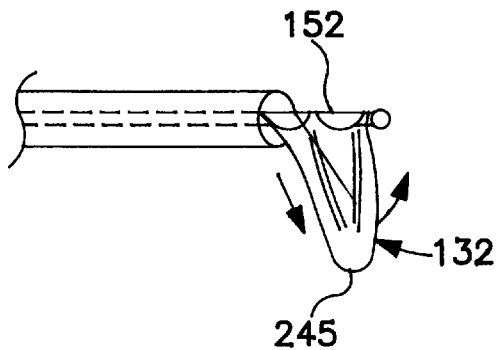
FIGS. 39 (A) through (D) show a partial outer periphery being formed in an angular progression.
Figure 39B:
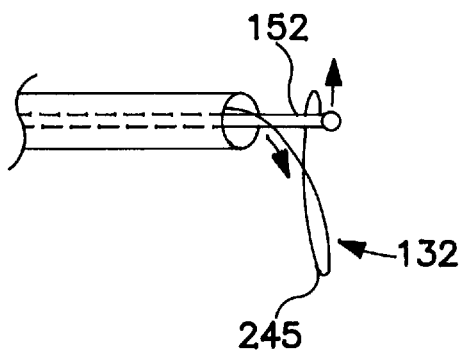
Figure 39C:
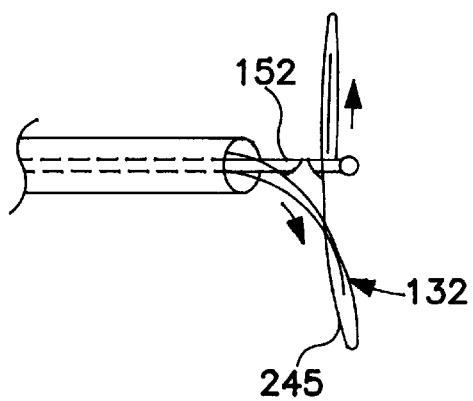
Figure 39D:
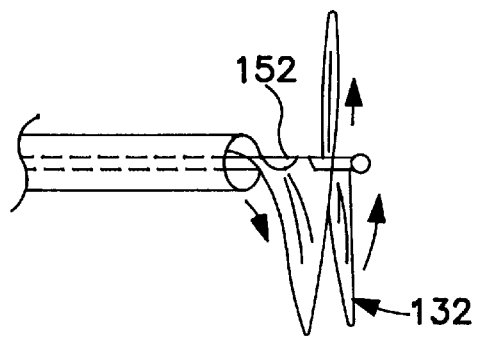
Figure 40A:
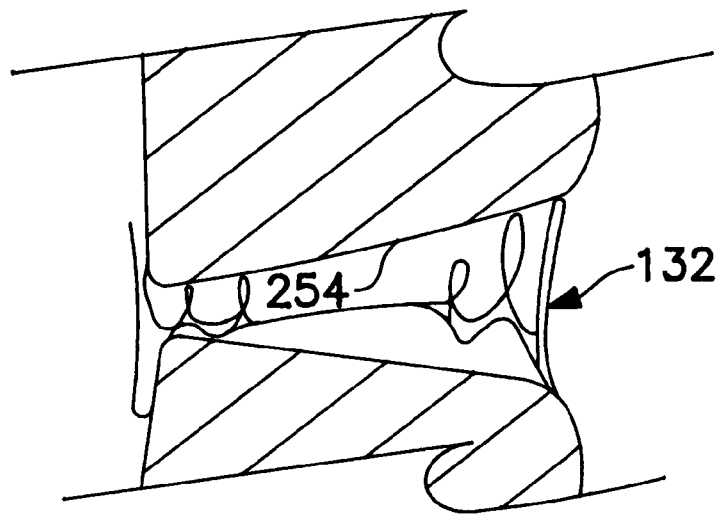
FIGS. 40 (A) through (D) show various forms of occlusion devices of the present invention.
Figure 40B:
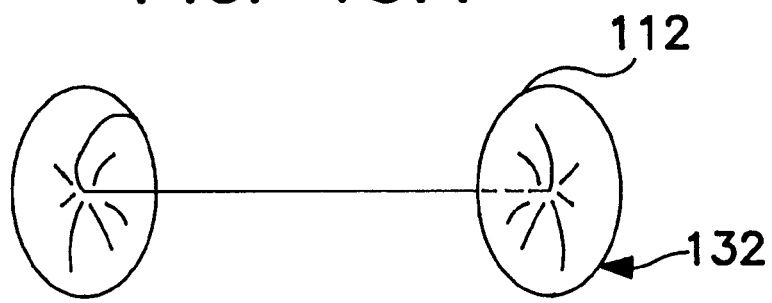
Figure 40C:
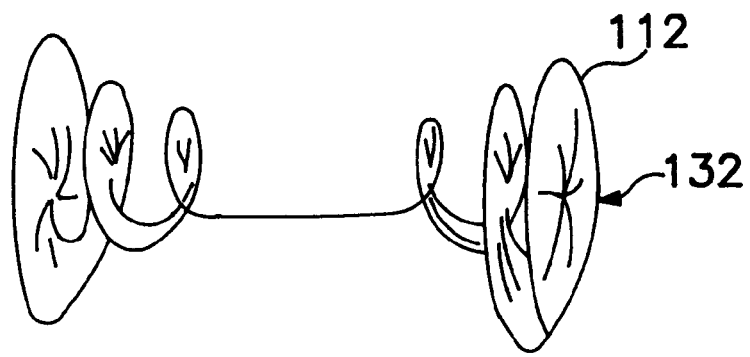
Figure 40D:
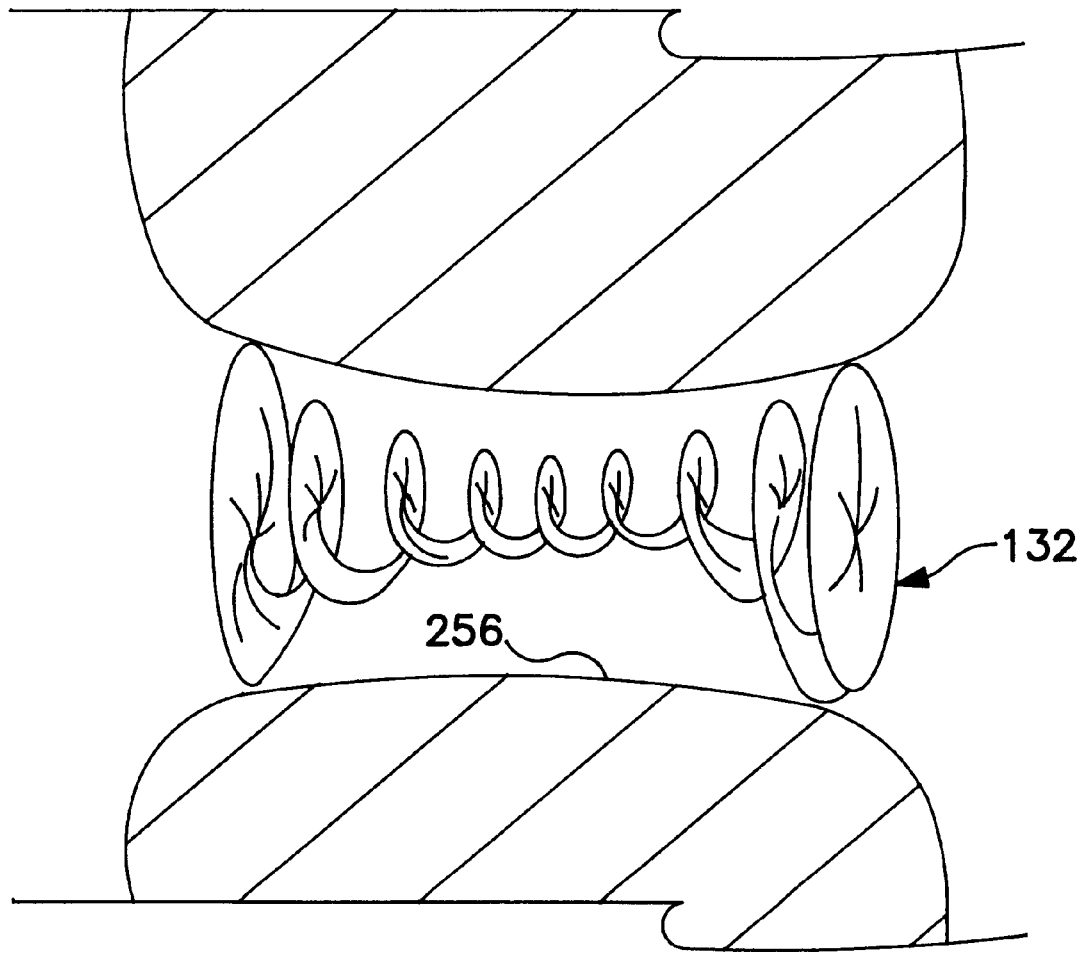

As shown in FIG. 37 and 38, the helical wire 112, has an elongated length when compressed into the insertion configuration. When the constraint is removed from the compressed helical wire, for example when the delivery catheter is retracted, the helical wire expands and forms an elastic support having a periphery. This periphery has a linear length. The deployed device also has a deployed length through the defect being repaired. As shown in FIG. 37 (A), the helical wire 112 has a distal end 230 and a proximal end 232. The length between the distal end 230 and the proximal end 232 is defined as the elongated length 234. As shown in FIGS. 37 (B) and (C), the deployed closure device 132 has a variable deployed length 236, 238 along the longitudinal axis, depending upon the width or wall thickness of the defect being repaired.

As shown in FIG. 38 (A), the expanded helical wire forms at least one outer periphery with a seal member or barrier 138 formed within this outer periphery. This outer periphery has a linear length 242. For a circular outer periphery, as shown in FIG. 38 (A), this outer periphery linear length 242, is approximately Pi times the diameter 240. If a second, or more than one outer periphery is formed, for example two peripheries as shown in FIG. 38 (A), an additional outer periphery is formed with an additional barrier 140 formed within this outer periphery. The total outer periphery linear length is the summation of the two or more individual outer periphery linear lengths. As shown in FIG. 38 (B), the formed outer periphery is not limited to circular shapes but can include stars, or any other shape that is adequate for the application for example triangles, squares or other polygons. These outer peripheries are not limited to closed or 360 degree or more forms, for example a semi-circle or crescent forms an outer periphery. As shown in FIG. 38 (B), the star shape has a outer periphery linear length 244, with a total outer periphery linear length of approximately two times the length of 244.

Various ratios can be calculated from these definitions of elongated length, deployed length and total outer periphery linear length. For example, assume a closure device has an elongated length of 10" and forms two, 360 degree circular outer peripheries each having 1.0" diameters. This device then has an elongated length to total outer periphery linear length ratio of approximately 1.6. A star shaped outer periphery device with an elongated length of 1", forming a total outer periphery linear length of approximately 2" has an elongated length to total outer periphery linear length ratio of approximately 0.5. Devices of the present invention can be configured to include ratios of elongated length to total outer periphery linear length of 0.70, 0.75, 0.80, 0.85, 0.90, 0.95,1.00,1.05,1.10, 1.15, 1.20, 1.25, 1.30, 1.35,1.40, 1.45, 1.50, 1.55, 1.60, 1.65,1.70,1.75, 1.80,1.85, 1.90, 1.95, 2.00, 2.05, 2.10, 2.15, 2.20 and larger.

As shown in FIGS. 39 (A) through (D), as the closure device 132 is progressively deployed, a partial outer periphery 245 is progressively formed. The helical wire expands and acts as an elastic support. This progressive formation of the partial periphery 245 occurs in an angular or sweeping sequence. Thus the outer periphery is formed progressively about a central or longitudinal axis extending through the defect. As shown in FIGS. 39 (A) through (D) this central axis is approximated by the lumen of the inner tube 152.

FIG. 40 (A) shows a cross section of an elongated defect 254. This elongated defect 254 can be occluded by the defect closure device 132. The elongated defect 254 can have various or different diameters along the defect cross section or along the longitudinal axis. An example of such an occlusion application is in the repair or occlusion of persistently patent ductus arteriosus.

As shown in FIGS. 40 (B) and (C), the elastic support or helical wire 112 can be configured into various shapes thereby occluding or obstructing the flow through various shaped defects or lumens.

FIG. 40 (D) shows a cross section of an elongated defect 256, having an approximately constant diameter along the defect cross section. The defect closure device 132 can be used to occlude or obstruct flow through this relatively constant diameter lumen. Examples of such uses include the occlusion or flow obstruction of vascular or tubular forms.

Figure 41A:
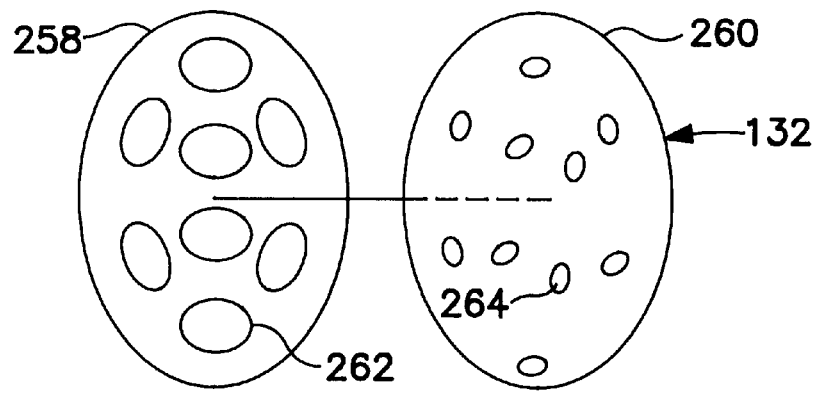
FIGS. 41 (A) through (C) show various forms of filter devices of the present invention.
Figure 41B:
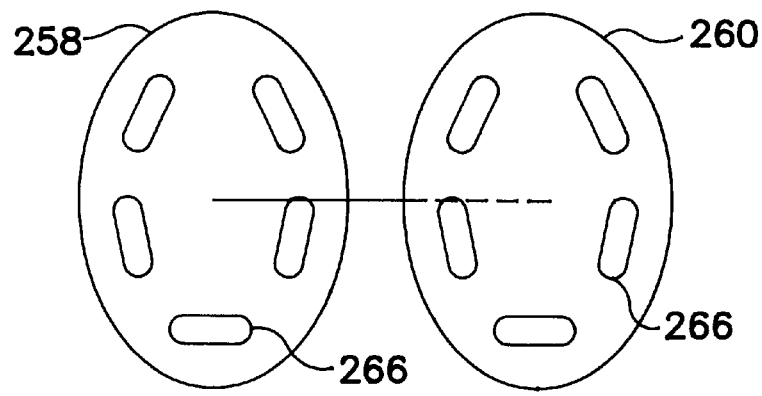
Figure 41C:
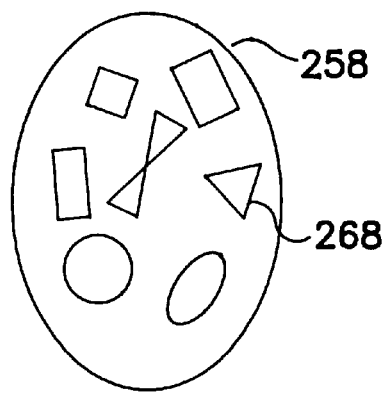

As shown in FIG. 41 (A), the defect closure device 132 can be used as a filter. A seal member 258 can be configured with flow through holes 262. Additional seal members, for example 260, can be configured to form a progressive filter having different openings 264 compared to the openings 262 in the first seal member 258.

As shown in FIG. 41 (B) the seal member openings 266 can include non-circular and elongated forms within the seal member 258 or 260.

As shown in FIG. 41 (C) the seal member openings 268 can be configured to include various sizes, shapes and orientations within the seal member 258.

Although, the present invention is preferred to close body defects like Atrial Septal Defects and Ventricular Septal defects, it can be used in other applications where the undesired communication or passage in the body exists. One specific example is Patent Ductus Arteriosis (PDA). PDA is a vessel which shunts aorta and pulmonary artery. This shunt is supposed to close immediately after childbirth. However, in certain congenital disease conditions, this vessel stays open after childbirth and hence leads to subsequent complications. It is desired to have a catheter based or thoroscopic device to block PDA. The present invention can be used for the PDA closure. Similarly, it can be used to block the flow in any tubular structure in the body such as fallopian tubes, arteriovenous fistula, etc.

In this respect, it should be appreciated that the present invention can be introduced in a wide variety of manners, including by merely using a tube ("catheter"), through thoracoscopic delivery, or other means. For small applications, it may be desirable to use pediatric sized catheters.

It should be appreciated from the foregoing description that an important benefit of the present invention, particularly the helically deployed embodiment, is that it can be restrained to a very compact insertion diameter and yet still fully expand to assume a full barrier to cover or seal a wall defect. This dramatic change in size is achieved by the ability of the elastic support of the present invention to assume a substantially elongated configuration in its insertion configuration and then automatically bend into another periphery of the closure device in its deployed configuration.

As the term "substantially elongated" is used herein, it is intended to encompass any orientation of the elastic support that stretches the support out longitudinally within a delivery tube. Preferably a "substantially elongated" support assumes nearly a straight line within the delivery tube; however, the term is intended to encompass any longitudinally disposed orientation, such as a stretched wire having one or more loops or kinks therein or even a support that may include two or more lengths of wire along its length.

The advantage of this construction is that the closure device can be compressed into very small tubes for delivery into tightly confined spaces. For instance, the closure device of the present invention will readily compact into a 9 French (F) catheter tube, and even much smaller tubes such as 8 F, 7.5 F, 7 F, 6.5 F, 6 F, 5.5 F, 5 F, 4.5 F, 4 F and even smaller.

A further advantage of this construction of the closure device of the present invention is that the device remains quite flexible in its compacted, insertion configuration. This is particularly true where the elastic support comprises only a single length of wire in its compacted state. This high degree of flexibility contributes to ease of manipulation of the device of the present invention, again assisting in deployment in tight confines.

Another way to express the advantages of the present invention is in the length of the insertion configuration of the present invention relative to the total length of the periphery of the device in its deployed configuration. Refer to detailed description of FIGS. 37 and 38 for further details.

This ratio is generally about 0.7 or more, and may include ratios of 0.8, 0.9, 1.0, 1.1, 1.2, 1.3, 1.4, 1.5 or more. Preferably the ratio is 0.7 or more.

Although the invention has been described in conjunction with specific embodiments, it is evident that many alternatives and variations will be apparent to those skilled in the art in light of the foregoing description and annexed drawings. Accordingly, the invention is intended to embrace all of the alternatives and variations that fall within the spirit and scope of the appended claims.

What is claimed is:

1. A closure device comprising the device having a compressed insertion configuration and an enlarged deployed configuration;

an elastic support, the support having a length and being substantially elongated in the insertion configuration and bending to form an outer periphery of the closure device in the deployed configuration;

a sheet attached along at least a portion of the length of the elastic support in the insertion configuration, the sheet forming a barrier within the outer periphery in the deployed configuration;

wherein the elastic support in the deployed configuration has a diameter of $d_1$ and the elastic support in the insertion configuration has a diameter of $d_2$, where the ratio of $d_1:d_2$ is greater than about 5:1.

2. The closure device of claim 1 wherein the closure device is contained within a tube in the insertion configuration, the tube being no more than 8 F in diameter.

3. The closure device of claim 1 wherein the elastic support bends helically when enlarging from the insertion configuration to the deployed configuration.

4. The closure device of claim 1 wherein the elastic support comprises a wire and the sheet is folded over the wire where attached along the length of the elastic support.

5. The closure device of claim 1 wherein the sheet comprises polytetrafluoroethylene.

6. A closure device comprising the device having a compressed insertion configuration and an enlarged deployed configuration;

an elastic support having a substantially elongated length in the insertion configuration and forming an outer periphery of the closure device in the deployed configuration;

the outer periphery of the closure device having a linear length;

a sheet attached along at least a portion of the length of the elastic support in the insertion configuration and forming a barrier within the outer periphery in the deployed configuration;

the length of the elongated elastic support relative to the total linear length of the periphery being a ratio of greater than about 0.7;

wherein the sheet is folded over the elastic support where the sheet is attached along the length of the elastic support.

7. The closure device of claim 6 wherein the closure device is contained within a tube in the insertion configuration, the tube being no more than 8 F in diameter.

8. The closure device of claim 6 wherein the elastic support bends helically when enlarging from the insertion configuration to the deployed configuration.

9. The closure device of claim 6 wherein the elastic support in the deployed configuration has a diameter of $d_1$ and the elastic support in the insertion configuration has a diameter of $d_2$, where the ratio of $d_1:d_2$ is greater than about 5:1.

10. The closure device of claim 6 wherein the elastic support comprises a wire and the sheet is folded over the wire.

11. The closure device of claim 6 wherein the sheet comprises polytetrafluoroethylene.

12. A closure device comprising
the device having a compressed insertion configuration and an enlarged deployed configuration;
an elastic support, the support having a length and being substantially elongated in the insertion configuration and bending to form an outer periphery of the closure in the deployed configuration;
the outer periphery being formed progressively about a central axis in an angular progression as the elastic support bends from the insertion configuration to the deployed configuration; and
a sheet attached along at least a portion of the length of the elastic support in the insertion configuration and forming a barrier within the outer periphery in the deployed configuration.

13. A closure device having a compressed insertion configuration and an enlarged deployed configuration comprising
at least one sealing member having a first edge and a second edge; and
means cooperating with the sealing member for enlarging during deployment the first edge into a peripheral edge; and
means cooperating with the sealing member for converging during deployment the second edge into a central edge;
wherein the sealing member forms a barrier in the deployed configuration extending between the central edge and the peripheral edge.

14. The device of claim 13 that further includes means for securing the central edge in a converged position.

15. The device of claim 14 that further includes
at least two sealing members; and
means for securing a first sealing member to a second sealing member in the deployed configuration.

16. A closure device comprising:
a) a membrane formed from at least one layer of material adapted to close a wall defect;
b) an elastic support attached to said membrane and adapted to extend the membrane into a barrier for closing the wall defect;
wherein the elastic support has a first deployed configuration with a longitudinal axis and a diameter of $d_1$ which is compressible into a second insertion configuration of a diameter $d_2$, where the ratio of $d_1:d_2$ is greater than about 5:1.

17. The closure device of claim 15 wherein said membrane includes at least two plies of cross-laminated biocompatible material.

18. The closure device according to claim 16 wherein said elastic support is a wire.

19. The closure device according to claim 18 wherein said wire is helically shaped.

20. The closure device according to claim 19 wherein said helically shaped wire contains at least two complete revolutions about said longitudinal axis.

21. The closure device according to claim 18 wherein said wire is nitinol.

22. The closure device according to claim 18 wherein said wire has shape induced memory.

23. The closure device according to claim 16 wherein the elastic support forms two barriers adapted to seal two sides of a wall defect.

24. The closure device according to claim 23 wherein each of said barriers is star shaped, where arms of the star radially support said membrane.

25. The closure device according to claim 24 wherein each of said arms includes first and second legs connected at their distal ends to respective ends of an arcuate connector; and the arcuate connector extends over an angle of less than 360°.

26. The closure device according to claim 16 wherein said membrane is a fluoropolymer.

27. The closure device according to claim 26 wherein said fluoropolymer is a copolymer containing tetrafluoroethylene polymer.

28. The closure device according to claim 25 wherein said fluoropolymer is expanded polytetrafluoroethylene.

29. The method according to claim 28 wherein said fluoropolymer is expanded polytetrafluoroethylene.

30. The closure device of claim 15 wherein the membrane contains 4 to 8 plies.

31. A method of assembling a defect closure device comprising:
a) providing a first membrane;
b) locating a tube on said membrane;
c) folding and laminating said membrane about said tube;
d) inserting an elastic wire into said tube; and
e) removing said tube and heating said membrane to embed said elastic wire.

32. The method according to claim 31 that further comprises forming membrane from several plies of material that are cross-laminated to one another.

33. The method according to claim 31 that further comprises providing nitinol as wire.

34. The method according to claim 31 that further comprises providing as the wire a material that has a memory induced configuration.

35. The method according to claim 34 that further comprises providing a wire with a memory induced helical configuration.

36. The method according to claim 31 that further comprises providing a fluoropolymer material as the membrane.

37. The method according to claim 36 wherein said fluoropolymer material is a tetrafluoroethylene polymer.

38. A closure device comprising
the device having a compressed insertion configuration and an enlarged deployed configuration;
an elastic support having a substantially elongated length in the insertion configuration and forming an outer periphery of the closure device in the deployed configuration;
the outer periphery of the closure device having a linear length;
a sheet attached along at least a portion of the length of the elastic support in the insertion configuration and forming a barrier within the outer periphery in the deployed configuration;
the length of the elongated elastic support relative to the total linear length of the periphery being a ratio of greater than about 0.7;
wherein the elastic support in the deployed configuration has a diameter of $d_1$ and the elastic support in the insertion configuration has a diameter of $d_2$, where the ratio of $d_1:d_2$ is greater than about 5:1.

39. The closure device of claim 38 wherein the closure device is contained within a tube in the insertion configuration, the tube being no more than 8 F in diameter.

40. The closure device of claim 38 wherein the elastic support bends helically when enlarging from the insertion configuration to the deployed configuration.

41. The closure device of claim 38 wherein the elastic support comprises a wire and the sheet is folded over the wire where attached along the length of the elastic support.

* * * * *

UNITED STATES PATENT AND TRADEMARK OFFICE
CERTIFICATE OF CORRECTION

PATENT NO.    : 6,080,182
DATED         : June 27, 2000
INVENTOR(S)   : Shaw et al.

Page 1 of 1

It is certified that error appears in the above-identified patent and that said Letters Patent is hereby corrected as shown below:

<u>Title page,</u>
Item [63] Related U.S. Application Data: Pat. No. "5,879,336" should read -- 5,879,366 --

Signed and Sealed this

Twenty-fifth Day of December, 2001

Attest:

Attesting Officer

JAMES E. ROGAN
*Director of the United States Patent and Trademark Office*